US011911499B2

(12) United States Patent
Trollsas et al.

(10) Patent No.: US 11,911,499 B2
(45) Date of Patent: Feb. 27, 2024

(54) SYSTEM AND METHOD FOR PROSTATE TREATMENT

(71) Applicant: RESURGE THERAPEUTICS, INC., San Jose, CA (US)

(72) Inventors: Olof Mikael Trollsas, San Jose, CA (US); John J. Stankus, San Jose, CA (US); Shahram Shawn Gholami, Monte Sereno, CA (US)

(73) Assignee: Resurge Therapeutics, Inc., San Jose, CA (US)

( * ) Notice: Subject to any disclaimer, the term of this patent is extended or adjusted under 35 U.S.C. 154(b) by 256 days.

(21) Appl. No.: 17/092,079

(22) Filed: Nov. 6, 2020

(65) Prior Publication Data

US 2022/0031606 A1    Feb. 3, 2022

Related U.S. Application Data

(60) Provisional application No. 63/081,865, filed on Sep. 22, 2020, provisional application No. 62/931,800, filed on Nov. 7, 2019.

(51) Int. Cl.
| | |
|---|---|
| *A61K 9/00* | (2006.01) |
| *A61K 31/00* | (2006.01) |
| *A61K 47/34* | (2017.01) |
| *A61K 47/22* | (2006.01) |
| *A61P 1/00* | (2006.01) |
| *A61K 31/337* | (2006.01) |
| *A61B 8/08* | (2006.01) |
| *A61K 31/436* | (2006.01) |
| *A61P 13/08* | (2006.01) |
| *A61K 45/06* | (2006.01) |
| *A61M 5/00* | (2006.01) |

(52) U.S. Cl.
CPC ............ *A61K 9/0019* (2013.01); *A61B 8/085* (2013.01); *A61K 9/0034* (2013.01); *A61K 31/337* (2013.01); *A61K 31/436* (2013.01); *A61K 45/06* (2013.01); *A61K 47/22* (2013.01); *A61K 47/34* (2013.01); *A61M 5/00* (2013.01); *A61P 13/08* (2018.01)

(58) Field of Classification Search
CPC .. A61K 9/0019; A61K 9/0034; A61K 31/337; A61K 31/436; A61K 47/22; A61K 47/34; A61M 5/00; A61P 13/08
See application file for complete search history.

(56) References Cited

U.S. PATENT DOCUMENTS

| | | | |
|---|---|---|---|
| 5,116,615 A | 5/1992 | Gokcen et al. | |
| 5,595,985 A | 1/1997 | Labrie | |
| 5,945,115 A | 8/1999 | Dunn et al. | |
| 6,177,404 B1 | 1/2001 | DeFeo-Jones et al. | |
| 6,277,391 B1 * | 8/2001 | Seo | A61K 9/5031 |
| | | | 424/501 |
| 6,689,803 B2 | 2/2004 | Hunter | |
| 6,759,431 B2 | 7/2004 | Hunter | |
| 7,008,633 B2 | 3/2006 | Yang et al. | |
| 7,015,253 B2 | 3/2006 | Escandon et al. | |
| 7,906,136 B2 | 3/2011 | Wong et al. | |
| 8,002,745 B2 | 8/2011 | Kaal et al. | |
| 8,133,491 B1 | 3/2012 | Selman et al. | |
| 8,313,763 B2 | 11/2012 | Margaron et al. | |
| 8,362,086 B2 | 1/2013 | Soll et al. | |
| 8,900,252 B2 | 12/2014 | Lamson et al. | |
| 9,186,464 B2 | 11/2015 | Franklin | |
| 9,545,464 B2 | 1/2017 | Roche et al. | |
| 9,814,685 B2 | 11/2017 | Baltezor et al. | |
| 10,004,813 B2 | 6/2018 | Hochberg et al. | |
| 10,159,683 B2 | 12/2018 | Wong et al. | |
| 10,265,477 B2 | 4/2019 | Schwab et al. | |
| 10,639,273 B2 | 5/2020 | Puri et al. | |
| 10,668,188 B2 | 6/2020 | Wang | |
| 10,792,427 B2 | 10/2020 | Metzner et al. | |
| 11,013,731 B2 | 5/2021 | Kundu et al. | |
| 11,097,061 B2 | 8/2021 | Gerlett | |
| 11,110,067 B2 | 9/2021 | Sharp et al. | |
| 2002/0055666 A1 | 5/2002 | Hunter et al. | |
| 2004/0002647 A1 | 1/2004 | Desai | |

(Continued)

FOREIGN PATENT DOCUMENTS

| | | |
|---|---|---|
| CN | 100431631 C | 11/2008 |
| EP | 1845942 B1 | 4/2014 |

(Continued)

OTHER PUBLICATIONS

Sartor, "Eligard 6: A New Form of Treatment for Prostate Cancer," European urology supplements 5: 905-910 (2006) (Year: 2006).*
Ahmed, "approaches to develop PGLA based in situ gelling system with low initial burst," Pak. J. Pharm. Sci. 28:657-665 (2015) (Year: 2015).*
International Search Report and Writetn Opinion of PCT/US2021/071538 dated Jan. 14, 2022; 12 pages.
Shikanov et al. "Intratumoral Delivery of Paclitaxel for Treatment of Orthotopic Prostate Cancer", Journal of Pharmaceutical Sciences, vol. 98, No. 3, Mar. 2009, pp. 1005-1014.
Ekaterina A. Lesovaya1, et al., Rapatar, a nanoformulation of rapamycin, decreases chemically-induced benign prostate hyperplasia in rats, Oncotarget, 2015, vol. 6, No. 12.

(Continued)

*Primary Examiner* — Julie Ha
*Assistant Examiner* — Kristina M Hellman
(74) *Attorney, Agent, or Firm* — SQUIRE PATTON BOGGS (US)

(57) ABSTRACT

A minimally invasive treatment of benign prostatic hyperplasia (BPH) tissue. A system includes a sustained release formulation comprising a cytostatic or cytotoxic drug, and an applicator or delivery system for local delivery of a composition comprising or consisting essentially of the sustained release formulation to the prostate. A method includes introducing a composition into the prostate to achieve a sustained release of the cytostatic or cytotoxic drug over a period of between about 14 days and 12 months.

24 Claims, 19 Drawing Sheets

(56) References Cited

U.S. PATENT DOCUMENTS

| | | | |
|---|---|---|---|
| 2005/0064045 A1 | 3/2005 | Zhong et al. | |
| 2006/0063732 A1 | 3/2006 | Vogel et al. | |
| 2006/0217680 A1 | 9/2006 | Barath | |
| 2007/0042046 A1 | 2/2007 | Saffie et al. | |
| 2007/0280992 A1* | 12/2007 | Margaron | A61K 9/0024 |
| | | | 514/291 |
| 2008/0194663 A1* | 8/2008 | Dunn | A61P 35/00 |
| | | | 514/397 |
| 2008/0286205 A1 | 11/2008 | Lennernas et al. | |
| 2008/0317736 A1 | 12/2008 | Franano | |
| 2009/0227633 A1 | 9/2009 | Damaj | |
| 2009/0248034 A1 | 10/2009 | Dolan et al. | |
| 2010/0081681 A1* | 4/2010 | Blagosklonny | A61K 31/675 |
| | | | 435/375 |
| 2013/0197446 A1 | 8/2013 | Gustafsson et al. | |
| 2013/0325143 A1 | 12/2013 | Lamson et al. | |
| 2014/0350516 A1 | 11/2014 | Schwab et al. | |
| 2015/0094667 A1 | 4/2015 | Verhoeven et al. | |
| 2015/0273117 A1* | 10/2015 | Wang | A61L 29/08 |
| | | | 604/517 |
| 2015/0322064 A1 | 11/2015 | Ren et al. | |
| 2016/0024099 A1 | 1/2016 | Ren et al. | |
| 2020/0101012 A1 | 4/2020 | Klein et al. | |
| 2020/0113820 A1 | 4/2020 | Pui et al. | |
| 2020/0170992 A1 | 6/2020 | Dizerega et al. | |
| 2022/0387731 A1 | 12/2022 | Diaz et al. | |

FOREIGN PATENT DOCUMENTS

| | | | | |
|---|---|---|---|---|
| WO | WO-2009060473 A2 * | 5/2009 | | A61K 9/0024 |
| WO | WO 2016/013829 A1 | 1/2016 | | |
| WO | WO 2018/128173 A1 | 7/2018 | | |
| WO | WO 2021050953 | 3/2021 | | |
| WO | WO 2023/147080 A1 | 8/2023 | | |

OTHER PUBLICATIONS

Rong-Fu Liu, Roles of autophagy in androgen-induced benign prostatic hyperplasia in castrated rats, Experimental and Therapeutic Medicine, 2018, 15: 2703-2710.

Lu, Jingxiao, Rapamycin-induced autophagy attenuates hormone-imbalance-induced chronic non-bacterial prostatitis in rats via the inhibition of NLRP3 inflammasome-mediated inflammation (Molecular Medicine Reports 19: 221-230, 2019).

Koshkin VS, Mir MC, Barata P, Gul A, Gupta R, Stephenson AJ, Kaouk J, Berglund R, Magi-Galluzzi C, Klein EA, Dreicer R, Garcia JA. Randomized phase II trial of neoadjuvant everolimus in patients with high-risk localized prostate cancer. Invest New Drugs. Jun. 2019;37(3):559-566. doi: 10.1007/s10637-019-00778-4. Epub Apr. 30, 2019. PMID: 31037562.

Yared JA, Tkaczuk KH. Update on taxane development: new analogs and new formulations. Drug Des Devel Ther. 2012;6:371-84. doi: 10.2147/DDDT.S28997. Epub Dec. 11, 2012. PMID: 23251087; PMCID: PMC3523563.

De Bono JS, Oudard S, Ozguroglu M, Hansen S, Machiels JP, Kocak I, Gravis G, Bodrogi I, Mackenzie MJ, Shen L, Roessner M, Gupta S, Sartor AO; Tropic Investigators. Prednisone plus cabazitaxel or mitoxantrone for metastatic castration-resistant prostate cancer progressing after docetaxel treatment: a randomised open-label trial. Lancet. Oct. 2, 2010;376(9747):1147-54. doi: 10.1016/S0140-6736(10)61389-X. PMID: 20888992.

Pal SK, Twardowski P, Sartor O. Critical appraisal of cabazitaxel in the management of advanced prostate cancer. Clin Interv Aging. Dec. 3, 2010;5:395-402. doi: 10.2147/CIA.S14570. PMID: 21152241; PMCID: PMC2998247.

Bode C, Trojan L, Weiss C, Kraenzlin B, Michaelis U, Telfel M, Alken P, Michel MS. Paclitaxel encapsulated in cationic liposomes: a new option for neovascular targeting for the treatment of prostate cancer. Oncol Rep. Aug. 2009;22(2):321-6. PMID: 19578772.

Non-Final office action of the U.S. Appl. No. 17/727,680 dated Aug. 25, 2022; 14 pages.

Final office action of the U.S. Appl. No. 17/727,680 dated Dec. 19, 2022; 13 pages.

Non-Final office action of the U.S. Appl. No. 17/727,675 dated Aug. 22, 2022; 7 pages.

Belz, Jodi Elizabeth, "Smart brachytherapy spacers for combined chemo-radiation therapy: local delivery of nanoparticles, chemotherapeutics, and molecular inhibitors for cancer treatment",. Diss. Northeastern University Boston, May 2017, 188 pages.

Brady et al., "A pilot study in intraparenchymal therapy delivery in the prostate: a comparison of delivery with a porous needle vs. standard needle", BMC Urology, 2018, 18:66, 8 pages. https://doi.org/10.1186/s12894-018-0378-8.

Cilurzo et al., "Injectability Evaluation: An Open Issue", AAPS PharmSciTech, vol. 12, No. 2, Jun. 2011, pp. 604-609; DOI: 10.1208/s12249-011-9625-y.

Dhingra N. and Bhagwat D., "Benign prostatic hyperplasia: An overview of existing treatment.", Indian J Pharmacol. Feb. 2011; 43(1):6-12; doi: 10.4103/0253-7613.75657. PMID: 21455413; PMCID: PMC3062123.

Le Broc-Ryckewaert et al., "Development of innovative paclitaxel-loaded PLGA nanoparticles: Study of their antiproliferative activity and their molecular interactions on prostatic cancer cells", International Journal of Pharmaceutics 454, 2013, pp. 712-719.

Watt et al., "Injectability as a function of viscosity and dosing materials for subcutaneous administration", International Journal of Pharmaceutics, vol. 554, 2019, pp. 376-386.

International search report and written opinion of PCT/US2023/011776 dated Jun. 13, 2023; 19 pages.

Non-Final Office action dated Jul. 27, 2023 for U.S. Appl. No. 17/727,680; 17 pages.

Cancaster—https://www.vitalitymedical.com/blog/selecting-syringes-and-needles.html; 2015.

Jackson et al., "The Suppression of Human Prostate Tumor Growth in Mice by the Intratumoral Injection of a Slow-Release Polymeric Paste Formulation of Paclitaxel", Cancer Research 60, pp. 4146-4151, Aug. 1, 2000.

* cited by examiner

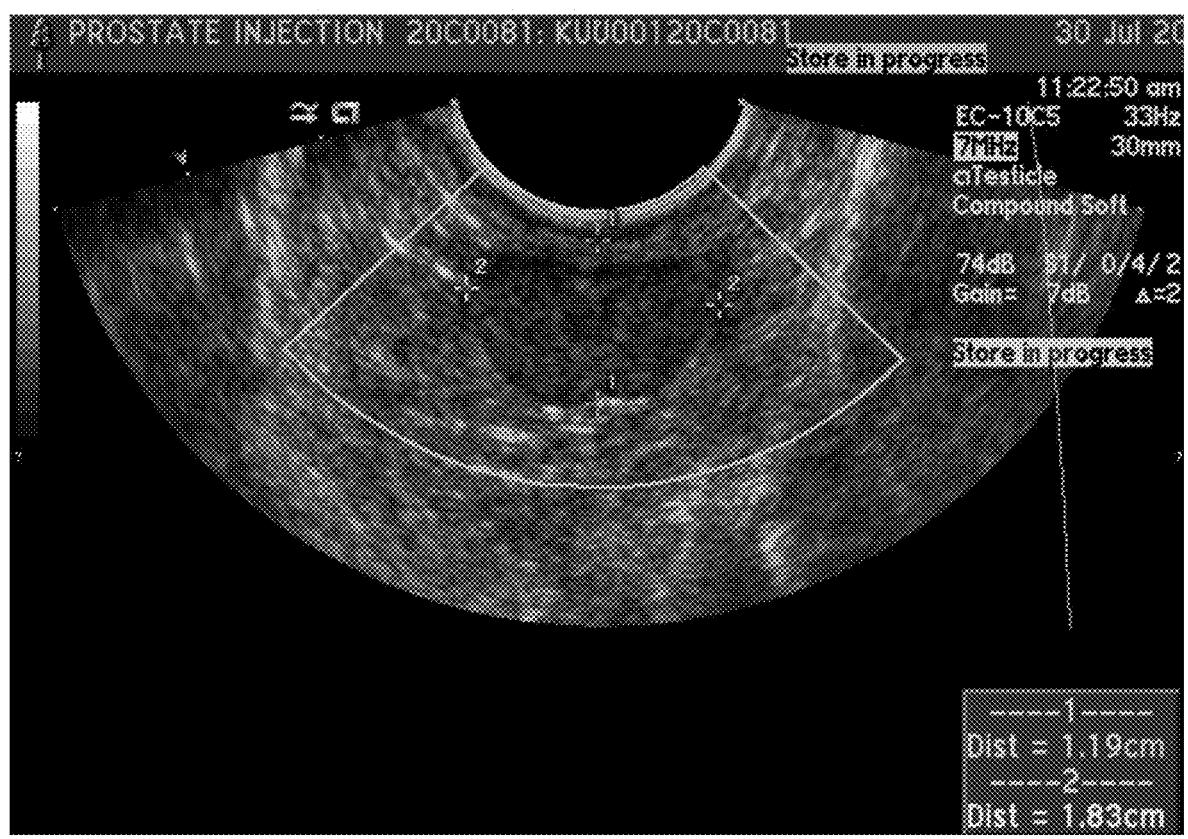
FIG. 8. Transrectal ultrasound volume measurement of the canine prostate in Animal#20C0081.

FIG. 9. Transrectal ultrasound with 20G 20cm Chiba biopsy needle.

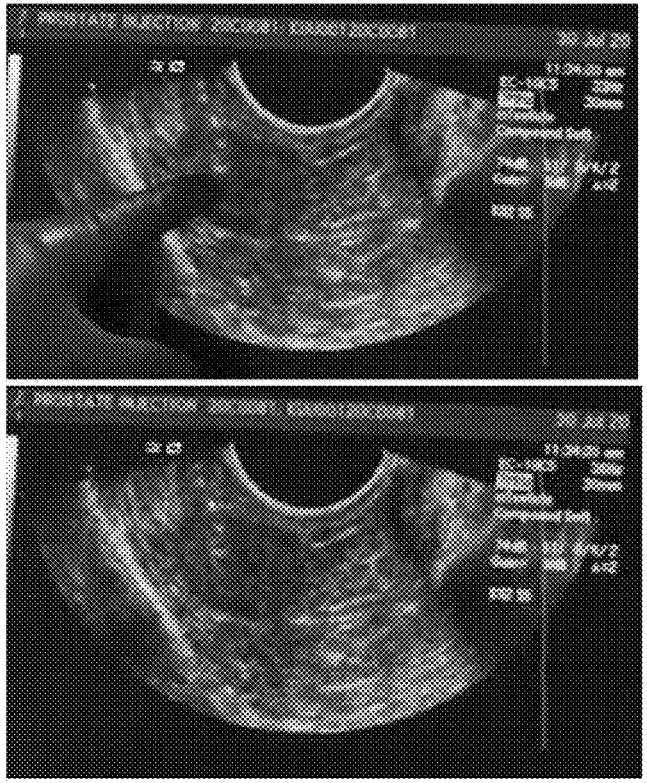
FIG. 10. RT-300 injectable as visible in canine prostate.
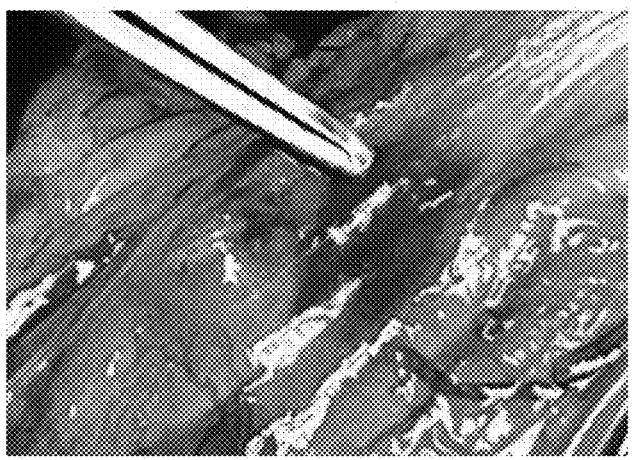
FIG. 11. Gross explantation of treated canine prostate showing visible presence of RT-300 injectate.

FIG. 12. Explanted bladder, prostate and urethra from Canine 20C0083 acute animal.

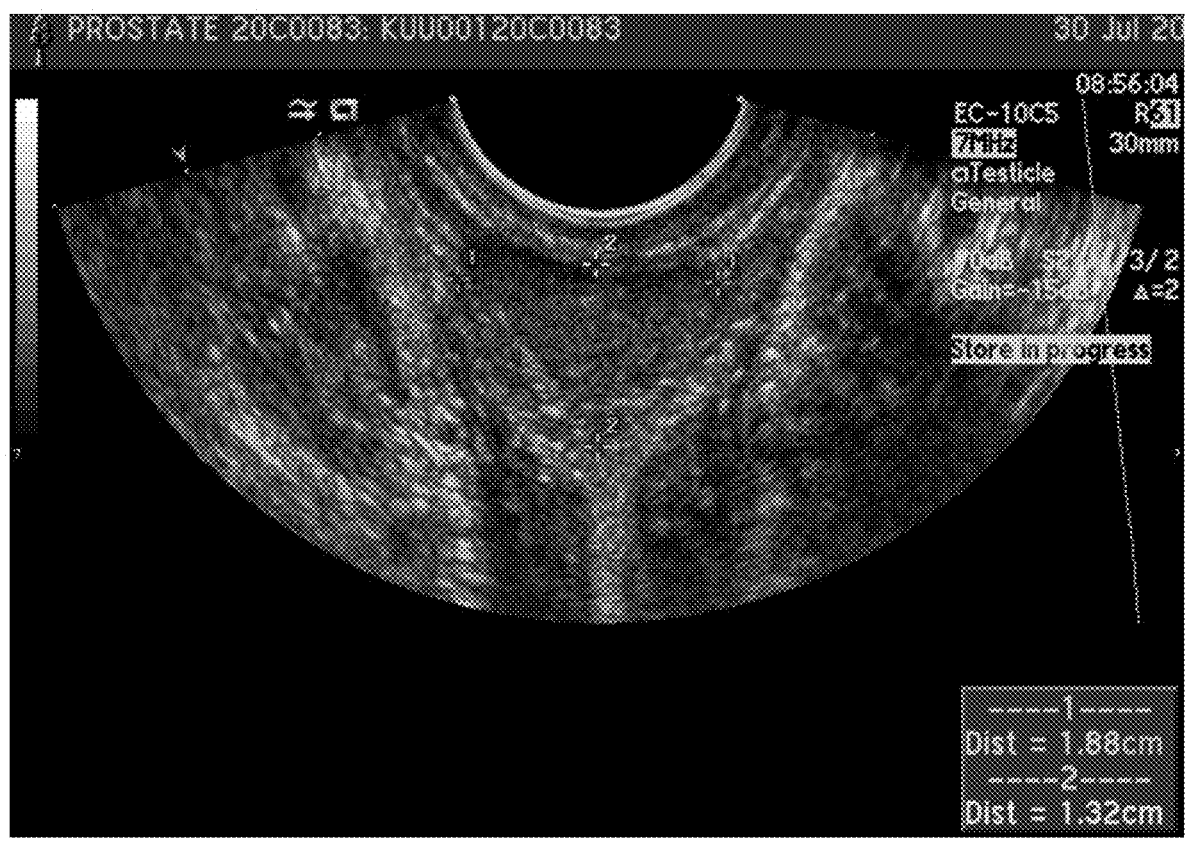
FIG. 13. Transrectal ultrasound volume measurement of the canine prostate in Animal#20C0083.

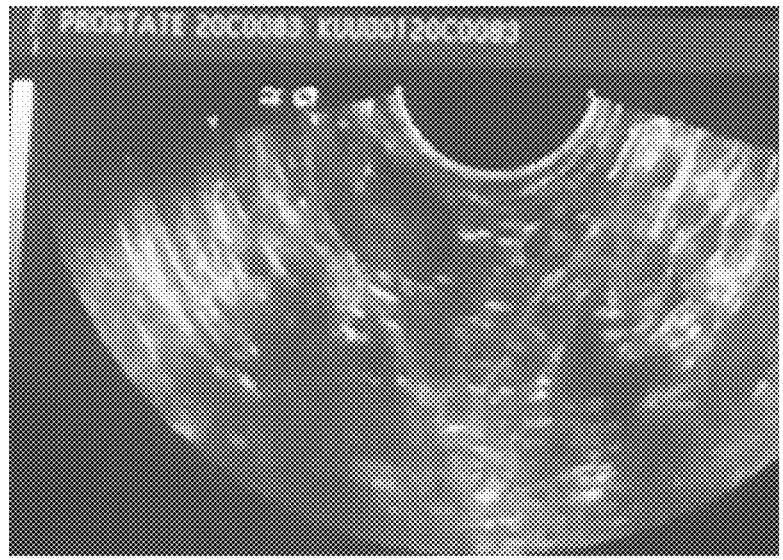
FIG. 14. RT-300 injectate visible in prostate per animal 20C0083.
FIG. 15. RT-300 injectate visible in prostate per animal 20C0083.

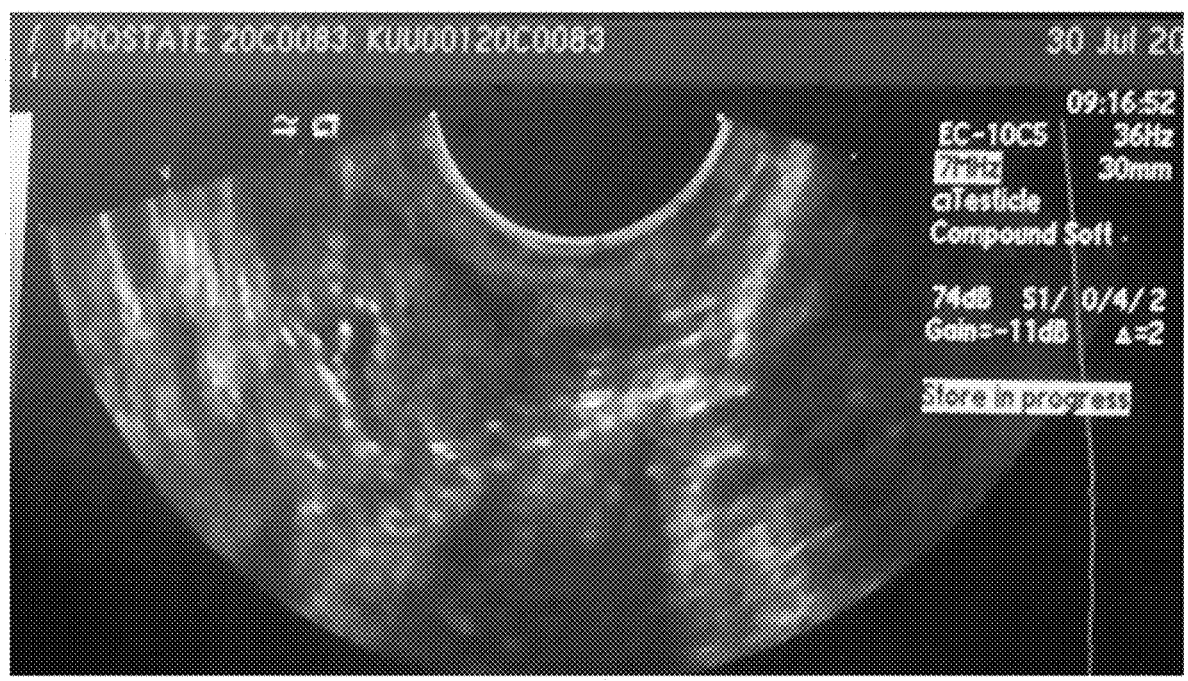
FIG. 16. RT-300 injectate visible in prostate per animal 20C0083.

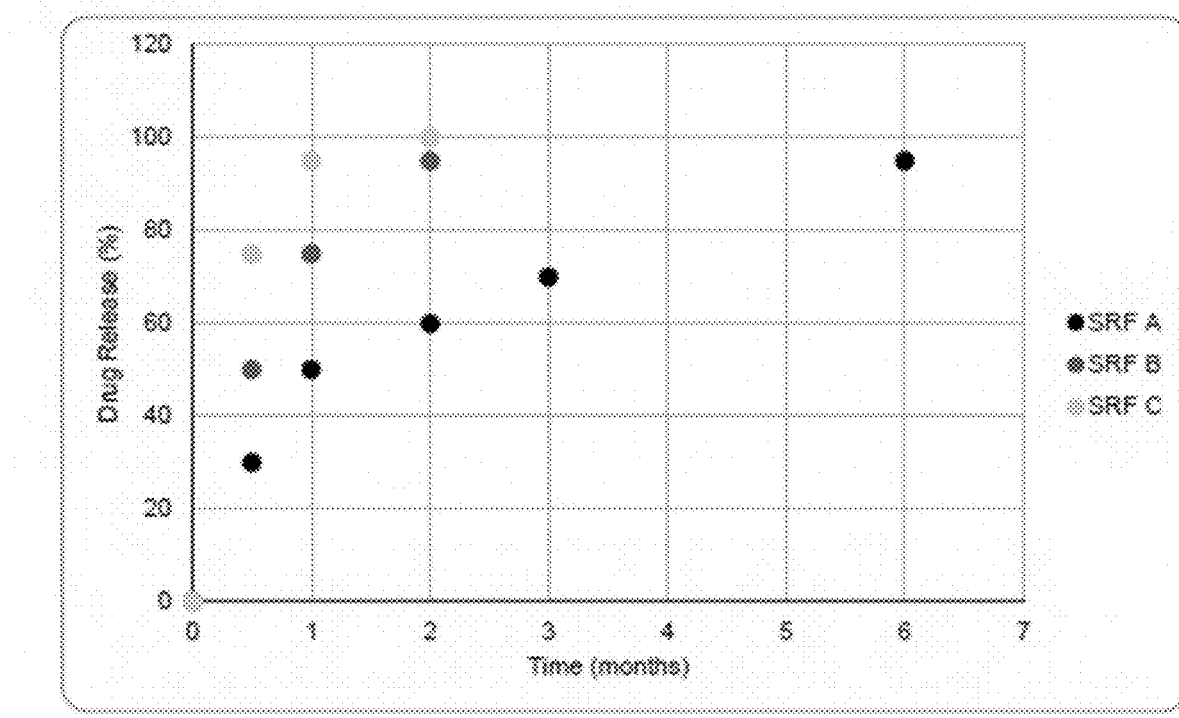
FIG. 17 - drug release vs. time

PROVISIONAL PATENT APPLICATION
Inventors:
Mikael Trollsas
John Stankus
Filed 11/6/19
SYSTEM AND METHOD FOR PROSTATE TREATMENT
DRAWINGS
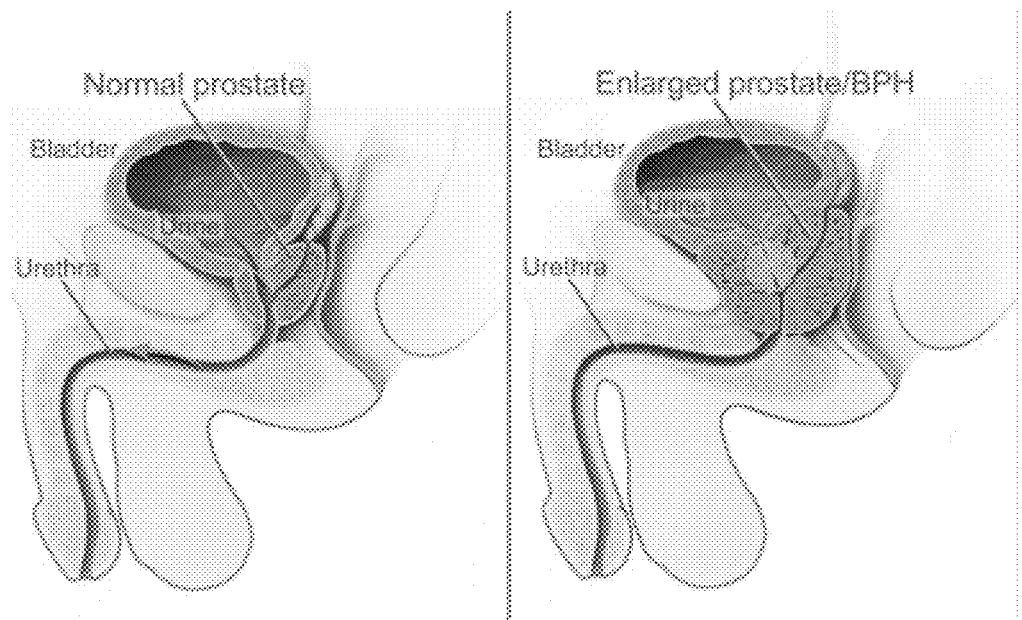
FIG. 18. Depiction of the enlarged prostate with benign prostatic hyperplasia (BPH).

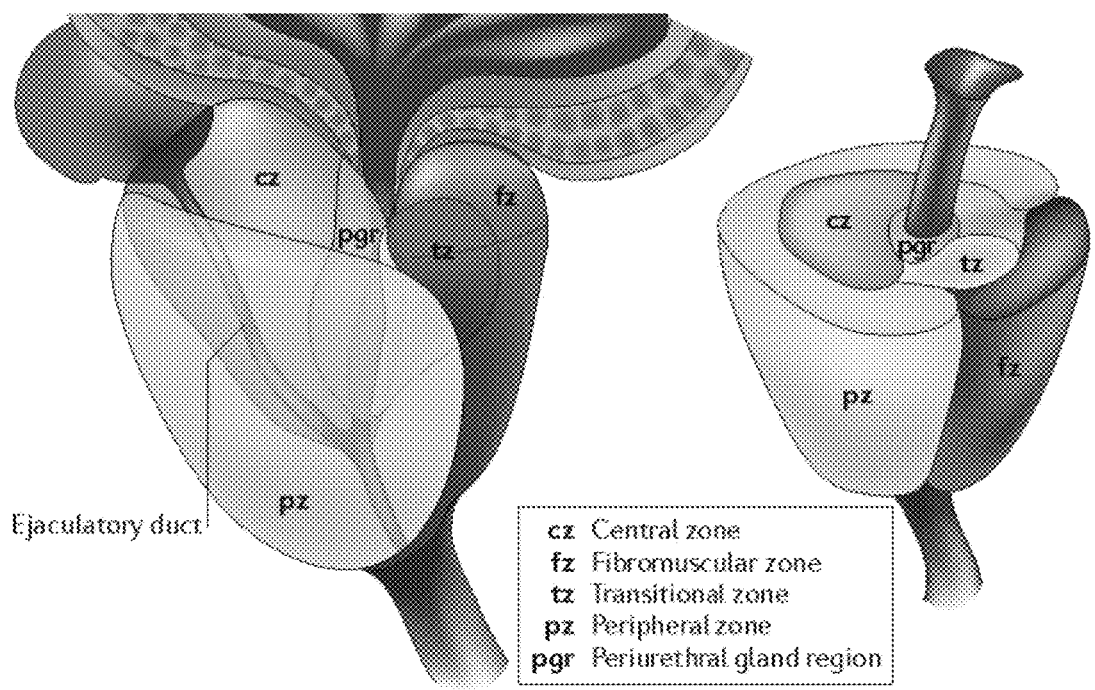
FIG. 19. Depiction of the prostate zone including the transitional zone primarily composed of smooth muscle cells.

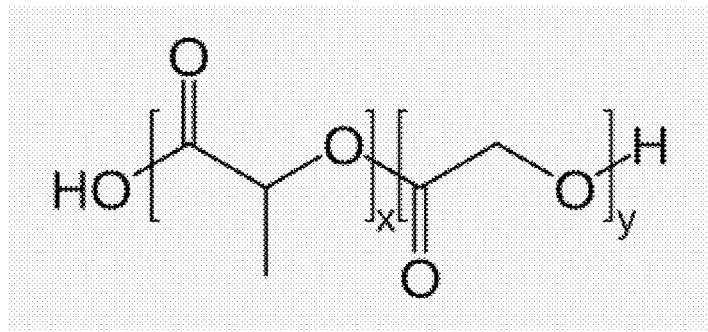
FIG. 20. Chemical structure of poly(lactide-co-glycolide) polymer.

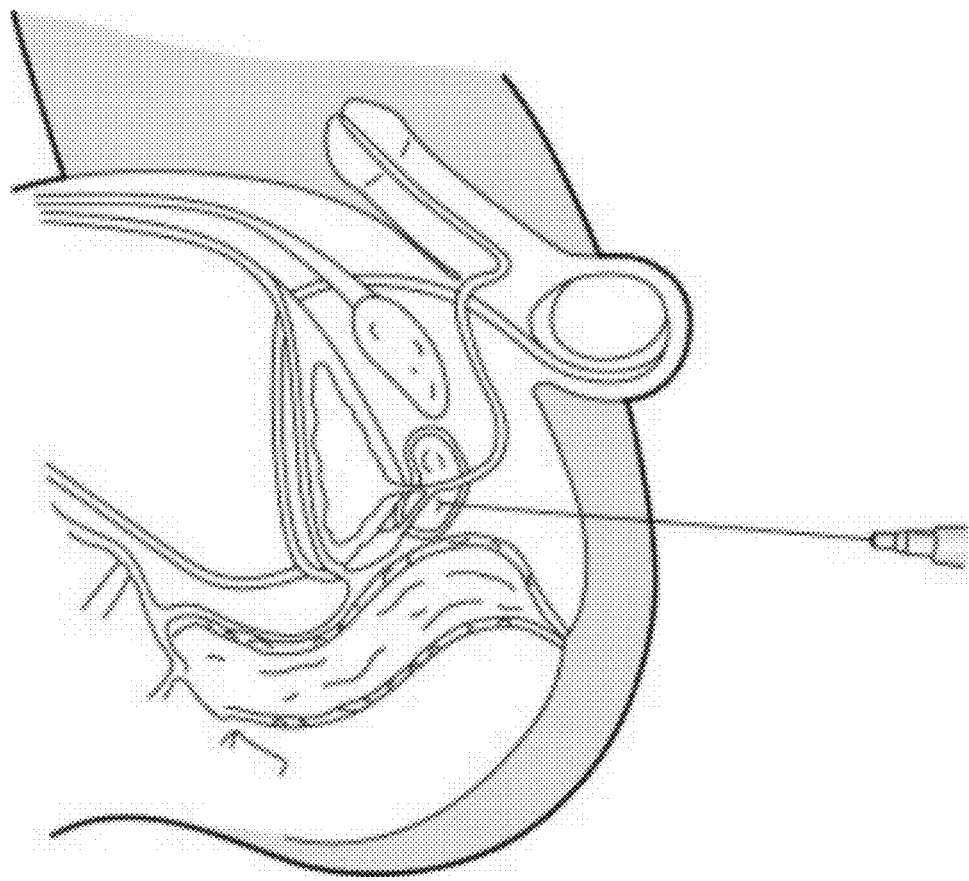
FIG. 21. Drawing depicting a transperineal delivery of drug in sustained release formulation using a needle based applicator or delivery device.

SYSTEM AND METHOD FOR PROSTATE TREATMENT

PRIORITY CLAIM

This application claims priority under 35 U.S.C. § 119(e) to U.S. provisional application No. 63/081,865, filed Sep. 22, 2020 (hereinafter RTPROV-2), the drawings and written specification of which are hereby incorporated by reference for all purposes, and U.S. provisional application No. 62/931,800 (hereinafter RTPROV-1), filed Nov. 7, 2019, the specification of which is hereby incorporated by reference for all purposes.

FIELD

Minimally invasive, local treatments for men's health and, more particularly, lower urinary tract symptoms.

BACKGROUND

Benign Prostatic Hyperplasia (BPH) is a noncancerous increase in size of the prostate gland due to proliferation of glandular epithelial tissue, smooth muscle and connective tissue within the prostate transition zone that causes lower urinary tract symptoms. Lower urinary tract symptoms (LUTS) include voiding or obstructive symptoms such as hesitancy, poor and/or intermittent stream, straining, feeling of incomplete bladder emptying, and storage or irritative symptoms such as frequency, urgency, urge incontinence, and nocturia. It affects approximately half of men aged 50 and over and by age 80, 90% of men are affected. Treatment options consist of lifestyle changes, medications, various procedures, and surgery. Lifestyle changes consist of weight loss, exercise, and decreased caffeine consumption. With more significant symptoms, oral medications such as alpha blockers (e.g. terazosin) or 5alpha-reductase inhibitors (e.g. finasteride) are prescribed. These medications, requiring daily dosing for patient compliance, may require a long onset to show efficacy, if at all, and carry side effects such as ejaculation changes, erectile dysfunction, weakness, headaches, and decreased libido.

There is an unmet clinical need to treat BPH with improved and sustained efficacy, administered via a less invasive procedure and with less associated side effects.

SUMMARY

In view of the foregoing, disclosed herein is an apparatus, method, and system for minimally invasive treatment of BPH, with sustained efficacy and less adverse side effects using a sustained release formulation.

The disclosure is generally directed to achieving a local delivery of a sustained efficacy treatment to the prostate (target tissue) and/or providing relief of urinary tract symptoms originating from, or associated with an enlarged prostate while mitigating if not avoiding damage to nearby prostate structures or the urethra. The treatment may be used by itself, or in combination with other known treatments.

Accordingly, in one aspect, a treatment of prostatic hyperplasia tissue, as provided herein, includes the delivery of a drug or multiple drugs to the tissue in a sustained release manner via the sustained release formulation. The treatment may be used with, or in addition to treatments involving removal of tissue, and/or delivery of energy to the tissue and additionally the administering of various agents.

A treatment for BPH according to the disclosure may include, for example, a mechanical treatment of the tissue (e.g., stenting, ballooning, thermal ablation, lasing, surgery), or delivery of pharmaceutical, biologic or chemical agents, drugs, including pharmaceutical, biologic, or chemical agents that may be delivered locally along with, or complimented with introduction of the sustained release formulation into the body. The sustained release formulation may additionally, or alternatively, be administered after a treatment of BPH according to other methods.

Access to prostatic tissue may be achieved transurethrally, transrectally or transperineally via an existing body orifice. It may be beneficial and less invasive to access the tissue by either transrectal or transperineal approaches. The advantages with a transrectal or transperineal approach include one or more (1) local anesthesia application instead of general anesthesia, (2) less trauma to the urethra tract and less resulting side effects also reducing the need for catheterization, (3) faster recovery time for the patient, (4) familiar treatment for the urologist physician similar to prostate cancer biopsy. For access by transrectal or transperineal approach, guidance may be provided by ultrasound, x-ray, computed tomography, magnetic resonance imaging or other imaging modality. Ultrasound imaging may be beneficial given that ultrasound is utilized for prostate biopsy. The transrectal approach closely mirrors the present prostate ultrasound and biopsy techniques familiar to urologists. Transrectal and transperineal approaches both avoid interaction with the urethra, which limits the caustic effects of urethral procedures therefore minimizing side effects and dysuria associated with currently available BPH procedures.

In another aspect, there is a delivery vehicle and sustained release formulation for delivery of a drug or a combination of drugs in an efficacious manner for treatment of the prostate. The drug may be an anti-inflammatory, anti-proliferative, cytoreductive, cytostatic, and/or cytotoxic that would affect the prostate size and gland proliferation. This delivery vehicle enables delivery of one or more drugs into the target tissue. Once delivered to the target tissue, the drug may then release in a slow, sustained release fashion, optionally delivered as an initial burst of the drug, followed by a slow, sustained release of the drug to the target release. As will be appreciated, the amount or lack of burst and/or the "slow, sustained release" release period will depend on the drug delivered to the prostate. In some embodiments a slow, sustained release may occur over, e.g., a 24-hour period, 3-7 days, 1-4 weeks, 1 to 12 months, 3 months, or 6 months.

In another aspect there is a system treating BPH including a delivery vehicle, the sustained release formulation, and imaging device for locating a target tissue of the prostate.

In another aspect there is an apparatus for treating BPH including a delivery vehicle adapted for being introduced into the body to introduce the sustained release formulation in liquid form to the tissue target.

In another aspect there is a method for treating BPH including injecting in or near the target tissue the sustained release formulation using a delivery vehicle.

In another aspect there is a sustained release formulation for treating BPH and deliverable to the targeted tissue using a needle or catheter, including a composition comprising the sustained release formulation.

In another aspect, there is a system, apparatus and method adapted for treatment of BPH by a needle injection of a SRF at a target tissue, the benefits of which may include one or more of a less invasive procedure leading to greater patient acceptance and less complications during patient treatment, less frequent procedures needed, and less risk of an administered drug or treatment producing adverse consequences for urinary or sexual function.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning consistent with the manner in which they are used in the present specification.

BRIEF DESCRIPTION OF THE DRAWINGS

FIG. 8 shows a transrectal ultrasound volume measurement of the canine prostate in Animal #2000081.

FIG. 9 shows a transrectal ultrasound with a 20 G 20 cm Chiba biopsy needle.

FIG. 10 shows an image of RT-300 injectable as visible in canine prostate.

FIG. 11 shows gross explanation of treated canine prostate showing visible presence of RT-300 injectate.

FIG. 12 shows explanted bladder, prostate and urethra from canine 2000083 acute animal.

FIG. 13 shows transrectal ultrasound volume measurement of the canine prostate in Animal #2000083.

FIG. 14 is an image of RT-300 injectate visible in the prostate of animal #2000083.

FIG. 15 is an image of RT-300 injectate visible in the prostate of animal #2000083.

FIG. 16 is an image of RT-300 injectate visible in the prostate of animal #2000083.

FIG. 17 shows a plot of Drug Release (%) as a function of time for SRF A, SRF B, and SRF C. Above the plot in FIG. 17 is a table showing Drug Release (%) for Formulation A, Formulation B, and Formulation C as a function of Time (months).

FIG. 18 shows a depiction of the enlarged prostate with benign prostatic hyperplasia (BPH).

FIG. 19 shows a depiction of the prostate zone including the transitional zone primarily composed of smooth muscle cells.

FIG. 20 shows the chemical structure of poly(lactide-co-glycolide) polymer.

FIG. 21 shows a drawing depicting a transperineal delivery of drug in sustained release formulation using a needle based applicator or delivery device.

DETAILED DESCRIPTION

Figure 1:
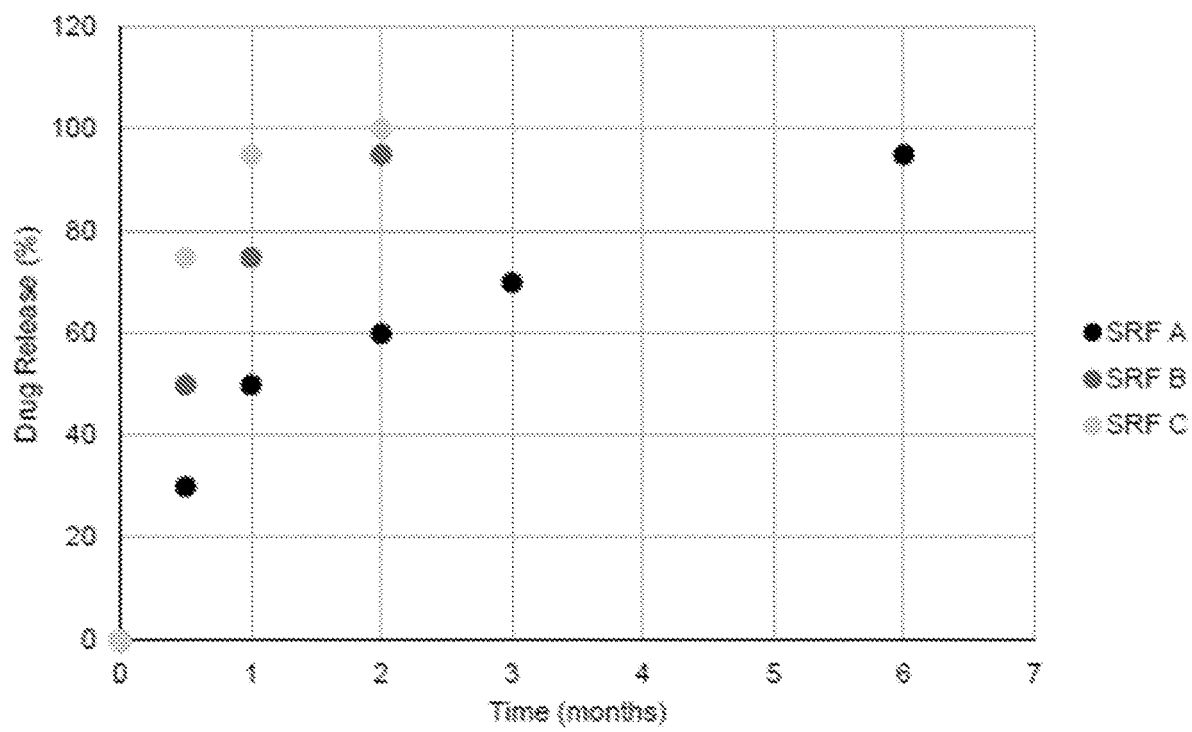
FIG. 1 shows Drug Release Curves for Sustained Release Formulations (SRFs) A, B and C.

For purposes of this disclosure, the following terms and definitions apply:

The following are examples of the polymer naming nomenclature appearing in the listing of additional disclosed embodiments following the detailed description. Other examples not explicitly spelled out here use the same rationale: PLGA8515A (0.3 dl/g) means poly(lactide-co-glycolide) with a monomer ratio of 85/15, end capped with acid groups (A), and an inherent viscosity of 0.3 dl/g; and PLGA6535E (0.5 dl/g) means poly(lactide-co-glycolide) with a monomer ratio of 65/35, end capped with ester groups (E), and an inherent viscosity of 0.5 dl/g; and Poly(lactide-co-glycolide) is typically poly(D,L-lactide-co-glycolide) but could also be e.g. any or a mixture of poly(D,L-lactide-co-glycolide), poly(D-lactide-co-glycolide), and poly(L-lactide-co-glycolide).

The terms "about" or "approximately" is defined herein as 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1. It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

The term "drug" or "agent" as used herein is defined as a therapeutic substance, other than food, used in the prevention, diagnosis, alleviation, treatment, or cure of disease. Unless stated otherwise, "drug" and "agent" shall have the same meaning.

The term "cytostatic" as used herein refers to a drug that is non-toxic to cells but does mitigate cell proliferation and permit cell migration. Cytostatic drugs may include without limitation rapamycin, sirolimus, everolimus, zotarolimus, myolimus, temsirolimus, tacrolimus, macrolide antibiotics, ridaforolimus, biolimus, novolimus, deforolimus, structural derivatives and functional analogues of rapamycin and any macrolide immunosuppressive drug. mTOR/PI3K dual inhibitors may also be utilized including dactolisib, BGT226, SF1126, PKI-587, and NVPBE235, mTORC1/mTORC2 dual inhibitors may also be utilized including sapanisertib, AZD8055, AZD2014 as derived from morpholino pyrazolopyrimidine.

The term "cytotoxic" as used herein refers to a drug that inhibits cell growth and proliferation such as chemotherapeutics. These drugs may include but are not limited to pactlitaxel, taxanes, protaxel, vincristine, etoposide, nocodazole, indirubin, anthracycline derivatives, daunorubicin, daunomycin, plicamycin, tauromustine, bofumustane, and plicamycin. These drugs may also be apoptotic such as TGF, topoisomerase inhibitors, including, 10-hydroxycamptothecin, irinotecan, and doxorubicin.

The term "composition" as used herein means a product of mixing or combining various elements or ingredients.

The term "sustained release formulation (SRF)" as used herein refers to a substance for treating BPH, the substance including a drug (or drugs) and carrier for the drug(s) or drug carrier comprising a polymer composition administered to the target tissue in liquid, gel or solid form using a delivery vehicle, whereupon local delivery to the target tissue the sustained release formulation is effective in producing a sustained release of the drug(s) to a targeted tissue of the prostate, thereby producing an efficacious result over a period of time, e.g., from about 1 to 12 months, or up to 2 years following treatment.

Drug or drug combinations used in the sustained release formulation include a cytostatic drug, cytotoxic drug, and/or other drugs. The other drug(s) may be used by themselves (i.e., the "other drug(s)" are the only active agents in the sustained release formulation), or in combination with the cytostatic drug or cytotoxic drug as part of the medical procedure for treatment of BPH. For example, the other drug(s) may be administered before a sustained release formulation including the cytostatic or cytotoxic drug is administered to the target tissue, included in the delivery vehicle with the sustained release formulation, which contains the cytostatic drug or cytotoxic drug administered to the target tissue, or administered after the sustained release formulation containing the cytostatic drug or cytotoxic drug is administered to the target tissue.

These other drugs, which may be administered with, or instead of the cytostatic or cytotoxic drug, include alpha blockers or 5-alpha reductase inhibitors. Alpha blockers may include terazosin, doxazosin, tamsulosin, alfuzosin, and silodosin. 5-alpha reductase inhibitors may include finasteride and dutasteride. Anti-inflammatory drugs may include but are not limited to corticosteroids such as dexamethasone, fluticasone propionate, triamcinolone acetonide, mometasone furoate, prednisone, hydrocortisone, estradiol, clobetasol, and budesonide. Non-steroidal drugs may include acetaminophen, ibuprofen, and naproxen. These other drug types may block cytokine activity or inhibit binding of cytokines to inhibit inflammatory signals such as anti-IL1, anti-IL 2, anti-IL3, anti-IL4, anti-IL8, anti-IL15, anti-IL 18, anti-MCP 1, anti-CCR2, anti-GM-CSF, anti-TNF antibodies and others.

Bioabsorbable refers to the disappearance of a compound into another substance. Biodegradable refers to cell mediated degradation resulting in cleavage of polymer molecular mass and generation of degradation by-products. Bioresorbable includes biodegradation and also total elimination by dissolution, excretion, or assimilation.

The term "target tissue" as used herein is defined as a tissue of the prostate tissue to include the transition zone, peripheral zone and central zone of the prostate, and the prostate. The term "dosage" as used herein is defined is the amount of the sustained release formulation administered to the target tissue using the delivery vehicle, the amount of the one or more drug(s) component(s) of the sustained release formulation, and/or the drug carrier, unless specified otherwise, and in an amount intended to produce a programmed, sustained release and efficacious outcome. This programmed, sustained release and efficacious outcome may be measured using the International Prostate Symptom Score (IPSS), or more generally relieving Lower urinary tract symptoms (LUTS) include voiding or obstructive symptoms such as hesitancy, poor and/or intermittent stream, straining, feeling of incomplete bladder emptying, and storage or irritative symptoms such as frequency, urgency, urge incontinence, and nocturia.

Five alpha reductase inhibitors reduce the prostate volume by 50% when given orally. Minimal reduction occurs in less than six months. An up to 50% reduction in prostate volume is expected in 12-24 months or possibly longer with appropriate therapy.

Alpha blockers can also be used to treat symptomatically at the time of procedure by blocking the alpha receptor and relaxing the prostate smooth muscle. Alpha blockers, five alpha reductase inhibitors or both may be co-formulated with cytostatic or cytotoxic drugs in the SRF.

When expressing a % of a substance in the SRF, the % of that substance may be expressed in terms of a percent weight of the drug(s) to the overall weight of the SRF ("% X by wgt"), or to the overall volume of the SRF ("% X by vol"). Unless stated otherwise the percent dosage % will, by default, always refer to a % by weight to the total measured SRF. Unless stated otherwise, weights are given in grams ("g") or milligrams ("mg"), molecular weight in kilo-Daltons ("kDa"), volume in microliters ("µL"), and viscosity units are expressed as inherent viscosity (i.e., the ratio of the natural logarithm of the relative viscosity to the mass concentration of the substance, such as a polymer. The unit of inherent viscosity is deciliters per gram (dL/g). A different measure of viscosity is intrinsic viscosity, which is a measure of a solute's contribution to the total viscosity.

The drug carrier portion of the SRF generally includes a polymer composition. A solvent, used in the preparation of the SRF, and/or other substances may also be present with the SRF, such as an ultrasound/echoing enhancing medium or other imaging enhancing depending on the imaging modality used.

The SRF may comprise 0.1-60% of a polymer composition, or more preferable 10-50% the polymer composition. The SRF may comprise 0-80% solvent. The drug to polymer weight ratio of the SRF may be 1:100, 1:50, 1:25, 1:20, 1:10, 1:5, 1:2, 1:1, 2:1, or 5:1. The SRF, once located at the target tissue, may release 1-10%, or 11-50% of the drug load in less than 24 hours, 24-72 hours, 3-7 days, 1-4 weeks, 1-3 months or more than 3 months. The SRF may release 80-100% in 24-72 h, 3-7 days, 1-4 weeks, 1-3 months or more than 3 months.

The drug carrier may be a polymer composition including silk-elastin like protein polymers, Pluronics F68 or F127 or a combination thereof, poly(ε-caprolactone) (PC), polylactides (PLA), poly(D,L-lactide) (PDLA), poly(ortho esters), polyanhydrides, polycarbonates, polyethylene glycol (PEG), polyethylene oxide (PEO), polyesteramides, and any combinations thereof including block and random co-polymers such as but not limited to poly(lactide-co-glycolide) (PLGA) and PLGA-PEG-PLGA. More specifically the PLGA composition may consist of poly(D,L-lactide-co-glycolide) (50:50), poly(D-lactide-co-glycolide) (50:50), poly(L-lactideco-glycolide) (50:50), poly(D,L-lactide-co-glycolide) (65:35), poly(D-lactide-co-glycolide) (65:35), poly(L-lactide-co-glycolide) (65:35), poly(D,L-lactide-co-glycolide) (75:25), poly(D-lactide-co-glycolide) (75:25), poly(L-lactide-co-glycolide) (75:25), poly(D,L-lactide-co-glycolide) (85:15) or a mixture thereof. The PLGA may be end-capped with ester, acid, alcohol, thiol or other end-groups. The inherent viscosity of the PLGA polymer may vary from 0.2 dL/g to greater than 1.0 dL/g. The molecular weight of the PLGA polymer may vary from 10 kDa up to 150 kDa. The polymer may be linear, branched, hyperbranched, dendritic, have a star structure, or be a dendrimer-like star polymer.

Additional embodiments of the drug carrier, SRF and composition follow.

The drug carrier may include a polymer composition including poly(lactide-co-glycolide), poly(D,L-lactide-co-glycolide), poly(D,L-lactide), ester end capped poly(D,L-lactide-co-glycolide) (50-50), ester end capped poly(D,L-lactide-co-glycolide) (65-35), ester end capped poly(D,L-lactide-co-glycolide (75-25), ester end capped poly(D,L-lactide-co-glycolide (85-15), acid end capped poly(D,L-lactide-co-glycolide) (50-50), acid end capped poly(D,L-lactide-co-glycolide) (65-35), acid end capped poly(D,L-lactide-co-glycolide) (75-25), acid end capped poly(D,L-lactide-co-glycolide (85-15), ester end capped poly(D-lactide-co-glycolide) (50-50), ester end capped poly(D-lactide-co-glycolide) (65-35), ester end capped poly(D-lactide-co-glycolide (75-25), acid end capped poly(D-lactide-co-glycolide) (50-50), acid end capped poly(D-lactide-co-glycolide) (65-35), acid end capped poly(D-lactide-co-glycolide (75-25), ester end capped poly(L-lactide-co-glycolide) (50-50), ester end capped poly(L-lactide-co-glycolide) (65-35), ester end capped poly(L-lactide-co-glycolide (75-25), acid end capped poly(L-lactide-co-glycolide) (50-50), acid end capped poly(L-lactide-co-glycolide) (65-35), acid end capped poly(L-lactide-co-glycolide (75-25), ester end capped poly(D,L-lactide-co-glycolide), acid end capped poly(D,L-lactide-co-glycolide), or combinations thereof.

The drug carrier may include a bioabsorbable polymer and the inherent viscosity of the polymer is between 0.2-1.0 dL/g, 0.2-0.6 dL/g, or 0.2 to 0.4 dL/g or 0.2 to 0.3 dL/g and the ratio of DL-lactide to glycolide is from 50/50 up to 90/10, 95/5, or 85/15.

The composition may include a bioabsorbable polymer at a concentration of 20-80%, 25-75%, 40-60% by wt. of the bioabsorbable polymer, 80-20%, 75-25%, 60-40%, by wt. of the solvent and 0.5%-30% by wt. drug; 1%-20% by wt. of drug, or 1%-5% by wt. of drug.

The drug carrier may generally be in the form of amorphous or semi-crystalline, homogenous, or phase-separated, and provided in the form of a liquid solution or, suspension, or as nanoparticles, microspheres or microparticles processed by spray drying, emulsion, electrospray, or extrusion. The biodegradable polymer is preferably chosen to substantially biodegrade in a period of about 3 to 6 months or 6 to 12 months.

In some embodiments it may be desirable to formulate the SRF so that the drug carrier is fully biodegraded before the next treatment, e.g., 6 months or 12 months after the prior treatment. For example, the polymer would have a ratio of glycolide to lactide of 50:50 up to 15:85 for a more hydrophilic property (faster degradation) and/or an inherent viscosity less than about 1.0 dL/g for a more hydrophilic property.

A polymer composition, when forming a constituent of the SRF, is a polymer composition that enables or achieves a desired "sustained release" of the one or more drugs to the target tissue. In some embodiments, the polymer composition enables or achieves at least 50%, or up to about 100%, or substantially all drug release between 30 and 90 days, through a combination of diffusion and degradation. In other embodiments up 100% of drug release occurs from 90 to 120 days from treatment. Preferably, there is an initial burst (e.g., up to 50% of drug) followed by a substantially reduced rate of release over the next following month, or several following months following treatment. For example, the drug has a release rate of between 5% to 50% during the first 24 hours from injecting the composition into the prostate and the drug has a release rate of no more than 10% to 75% over the first month, 25% to 95% over the first three months, and/or 50% to 100% over the first six months.

A programmed, sustained release of, e.g., from 1 to about 12 months, is achieved by selection of drug carrier (polymer structure) and/or modifying the morphology and mechanical properties (stiffness of the polymer), the polymer/drug ratio, controlling the physical shape/dimensions (volume) of the SRF and/or composition that is delivered to the target tissue. Other factors affecting the release rate include:

ability of polymer to swell (controlled by e.g. monomers selection and monomer ratios=polymer structure).
  porosity/morphology (controlled by e.g. polymer structure and concentration, polymer/solvent ratio and miscibility, and polymer/drug ratio—less drug than polymer than drug is trapped).
  how fast the materials gel and whether glass transition is reached—transition from liquid to solid using water soluble or insoluble solvents (fast gelation leads to faster initial release/burst) (controlled by e.g. polymer structure and concentration, polymer/solvent ratio and miscibility).
  drug/polymer miscibility and polarity of solvent, and
  molecular weight and lipophilicity of drug.

The sustained release formulation has to keep drug exposure near the prostate and minimize leak or flow to other surrounding organs. In addition, the SRF should not take up too much volume in the prostate. A desired shape of the drug release curve could be a burst of drug and early tissue exposure for fast efficacy and then plateau of drug over 3-6 months for sustained efficacy.

Fast/burst release with N-methyl pyrrolidone (NMP) solvent—water soluble; advantage to have a large release within the first 24 hours, or within the first 1 week, or two weeks; then a reduced rate of release afterwards.

FIG. 1 shows a Drug Release Curve for Sustained Release Formulation (SRFs) A, B and C. These exemplary SRFs provide a burst followed by gradual release of drug over a period of up to 6 months. SRF A releases about 25% of the drug within the first month, followed by a slow, gradual release where about 95% is released at six months. SRF B has an initial burst of about 50% within the first month, followed by about 100% release at two months. SRF C has an initial burst of about 75% within the first month, with about 100% release at about two months.

TABLE 1 below shows examples of SRF formulations for each of SRF A, B and C. Examples A1, A2 exhibit approximately the same release rate characteristics as SRF A in FIG. 1. Examples B1, B2 exhibit approximately the same release rate characteristics as SRF B in FIG. 1. Examples C1, C2 exhibit approximately the same release rate characteristics as SRF C in FIG. 1.

TABLE 1

Species of SRF formulations for SRF A, B and C in FIG. 1

| SRF | polymer | drug | % vol. drug v. polymer | solvent |
|---|---|---|---|---|
| A1 | PLGA8515 | Sirolimus | 1-2% drug, 50% polymer | NMP |
| A2 | PLGA8515 | Pactlitaxel | 1-2% drug, 50% polymer | NMP |
| B1 | PLGA7525 | Sirolimus | 3-5% drug, 45-47% polymer | NMP |
| B2 | PLGA7525 | Paclitaxel | 3-5% drug, 45-47% polymer | NMP |
| C1 | PLGA5050 | Sirolimus | 10-20% drug, 30-40% polymer | NMP |
| C2 | PLGA5050 | Paclitaxel | 10-20% drug, 30-40% polymer | NMP |

TABLE 2 plotted ranges for SRF A, B & C (FIG. 1)

| Time (months) | SRF A (drug release %) | SRF B (drug release %) | SRF C (drug release %) |
|---|---|---|---|
| 0 | 0 | 0 | 0 |
| 0.5 | 30 ± 20 | 50 ± 25 | 75 ± 25 |
| 1 | 50 ± 20 | 75 ± 15 | 95 ± 5 |
| 2 | 60 ± 15 | 95 ± 5 | 100 |
| 3 | 70 ± 10 | | |
| 6 | 95 ± 5 | | |

The SRF may be delivered to the target tissue in the form of a composition in liquid form (i.e., the SRF's drug(s) and drug carrier are in solution, or in suspension in a solvent when in the delivery vehicle) or as a composition in gel form, either upon contact with water at the target tissue, or as formulated and contained within the needle or catheter. The later examples of a composition including the SRF may be made by dissolving the SRF in a suitable solvent. Suitable solvents for these embodiments include water, N-methylpyrrolidone (NMP), dimethyl sulfoxide (DMSO), 2-pyrrolidone, propylene carbonate, caprolactam, triacetin, alcohols, benzyl benzoate, ethyl acetate, triethyl citrate, benzyl alcohol, glyme (dimethoxyethane), diglyme, and other glycol ethers, and dichloromethane, or any mixture thereof.

The composition should be formulated at a concentration and viscosity permitting passage in a 16 G or larger inner diameter needle applicator. Drug to polymer ratios may vary from 0.05 to 2.0. Drug and polymer concentrations in solvent may range from 0.1 wt % up to 60 wt %. Injection volumes of the drug portion of the SRF may range from 25 microliters up to 5 mL per injection. Overall dosage of drug provided in the SRF can range from 50 mcg up to 200 mg. For example, a composition containing the SRF is 300 mcg of everolimus or paclitaxel dissolved with 300 mcg ("mcg"—micrograms) poly (D, L-lactide-co-glycolide) (85:15) in NMP at a 50 wt % concentration.

The gel-like properties of some compositions may be beneficial to prevent infection from the rectal area along the needle tract. A sufficiently high viscosity can keep the drug in place, mitigating the possibility that the drug travels through the insertion pathway from target tissue to entry point. In this sense the gel-like composition acts as a sealant.

A gel-like state for the composition (as delivered or after delivery) is believed advantageous because once delivered to the target tissue, the SRF will tend not to dissipate or diffuse to other non-intended treatment areas of the prostate of adjacent tissue. As such, the dosage may be lower when the SRF exists in a gel-like form at the target tissue. More generally, it may be desirable to formulate the SRF to exhibit a high viscosity (e.g., gel-like) but not so high as to impair the ability for a physician to deliver the SRF to the target tissue for similar reasons.

Alternatively, the composition may be adapted to foam when located at the target tissue.

The sustained release formulation may alternatively be provided in the form of rods provided by melt or solvent casting, fiber spinning, electrospinning, injection molding or extrusion. For extrusion the drug of the SRF must be stable at the extrusion temperature necessary to melt the polymer. For example, paclitaxel (melting point approximately 216° C.) may be mixed at 60 wt % in poly(D,L-lactide-co-glycolide) (85:15) and extruded using a twin screw compounder at less than 200° C. above the glass transition at which the amorphous polymer flows through a die to form rods then cut to length. Alternatively everolimus (melting point approximately 100° C.) may be mixed at 60 wt % in polycaprolactone and extruded using a twin screw compounder at less than 100° C. or higher temperature above glass transition at which the polymer flows through a die to form rods then cut to length. To enhance the mixing, the drug and drug carrier may be premixed by methods such as spray drying, emulsion, electrospray, extrusion, solvent casting, melt casting. Alternatively, the polymer resin granules and drug powder may be mixed. Particle size reduction may be feasible by known methods such as milling, jet milling, spray drying, electrospray, emulsion, and/or cryogenic methods.

The following disclosure provides examples including non-limiting embodiments of invention for treating prostatic hyperplasia tissues within a patient. Local drug delivery is in the form of the sustained release formulation providing sustained delivery of a cytostatic or cytotoxic drug delivered using a delivery vehicle to the patient. The delivery vehicle may be in the form of a needle or catheter administered by a health professional.

The local drug delivery device applicator may be a needle or catheter for delivery of the composition including the SRF to the target tissue. An applicator portion of the delivery vehicle may include a chamber for holding the drug and drug carrier separate from each other, a mixing element for combining the drug and drug carrier such as a static mixing Y-adapter. Alternatively, the drug and drug carrier may be mixed using two syringes connected with an adapter, with back and forth plunging to mix the drug and drug carrier. The applicator needle or catheter, and/or other component may be imaged under ultrasound to visualize the therapy. Echogenicity may be enhanced by dimpling of the applicator needle or coatings. Echogenicity may also be enhanced by incorporation of contrast enhancing agents such as microbubbles, sulfur hexafluoride, octofluoropropane, air, lipid and/or albumin shells. The applicator may have components for attachment to a rectal ultrasound probe. The applicator may have markings demonstrating measurement of lengths of needle insertion. The applicator may have a user-friendly handle and plunger to deliver the needle or catheter to the target tissue. An applicator needle may range from 16 G up to 25 G. The needle length may be 40 cm or less (e.g. 20 cm length) in order to reach the target tissue from a transrectal or transperineal approach.

The various advantages of the invention described herein may be, as mentioned earlier, practiced in the form of stand-alone treatment or in combination with a known treatment for BPH administered before, during or after such treatment. Those known treatments for BPH may include balloon dilation, stenting, transurethral incision, transurethral resection (TURP), transurethral needle ablation, transurethral microwave therapy, electrical vaporization, water vapor thermal therapy, prostatic urethral lift (PUL) implants, etc.

The known procedures have demonstrated varying levels of efficacy, as well as undesirable or adverse indications, complications associated with the invasive aspects of the treatment, and/or negative patient experiences. TURP produces improved efficacy and improvement in urinary flow rate and symptom score (IPSS) but is invasive with significant side effects on incontinence, urgency, dysuria, acute retention, stricture, ejaculation dysfunction and sexual dysfunction. Water vapor therapy and PUL have demonstrated less sexual dysfunction side effects but are limited to use in smaller BPH prostates less than 80 ml and have shown less efficacy with non-responders and higher retreatment rates compared to TURP. Furthermore, all procedures are invasive and require transurethral access and catheter placement.

Less invasive targeted drug delivery approaches to the prostate zone have been attempted by the transrectal or transperineal routes such as pore forming proteins and peptides in saline formulations with single dosages but demonstrated limited efficacy versus saline placebo in randomized clinical trials. See Indian J Urol. 2008 July-September; 24(3): 329-335. doi: 10.4103/0970-1591.42613, PMCID: PMC2684358, PMID: 19468462; Injection therapy for prostatic disease: A renaissance concept Arash M. Saemi, Jeffrey B. Folsom, and Mark K. Plante. Additionally, alcohol or medications injected into the prostate have been ineffective. Alcohol single injection is very caustic and poorly controls the area of delivery. Medication injection into the prostate is also ineffective as it is given in a single dose with poor effect. Other attempts to treat prostate using similar drugs have been used, such as drugs taken orally, or if injected, the injectate did not include a sustained release formulation of the drug and thus an efficacious response in the target tissue injected would not be exhibited.

A delivery of the SRF to the target tissue as described, may also be used with, prior to, or after delivery of a drug eluting implant or stent designed to maintain patency of the urethra. This implant may be composed of nitinol or bioabsorbable polymers such as PLGA. The implant may be delivered by a transurethral, transrectal or transperineal approach. The implant may consist of a shape set nitinol wire or extruded polymer fiber that is then coated with drug in a sustained release formulation by dip, air assisted, ultrasonic or electrospray coating. The design may be such that the implant corkscrews around the urethra transition zone and does not impact the lumen of the urethra to minimize adverse effects and side effects.

The SRF may also be used in a complementary manner with an implantable energy generator to deliver direct energy in a continuous or pulsed manner by activation of external stimuli. The energy generator may relieve lower urinary tract symptoms by neuromodulation of the target tissue.

Examples

A clinical study was conducted to evaluate the safety and efficacy of a composition comprising a sustained release formulation (hereinafter "RT-300") injected into the prostates of two canine models, each having normal (non-enlarged) prostates. 0 and 28 days following the procedure the models ("animal #2000081", the acute model/animal) were humanely euthanized and evaluated to determine whether there were any acute, toxic effects of the injectate.

The day to day behavior of the second model ("animal #2000083", chronic model/animal) was being studied over the 28-day period following the procedure.

Data collected from each of the models (i.e., the acute and 28-day study):
Evaluate Prostate Morphology and Measure Prostate Size/Weight Baseline and Post-Treatment (Ultrasound)
Urinalysis, Volume Output and Residual at baseline, post treatment, daily to Termination
Gross Necropsy and Camera/Microscope Imaging at Termination, Fixation
Histology at Treatment Site at Termination (H&E, TUNEL optional line item)
Clinical pathology at baseline and termination (optional line item)

RT-300 is a composition including a sustained release formulation prepared by adding 0.5 mL N-methyl pyrrolidone (NMP) to a vial with 0.25 g paclitaxel and vortexed until dissolved and then taking 100 microliter of that drug solution and add to 2.5 mL of a 50/50 PLGA8515 NMP solution using syringe to syringe mixing with a female to female luer connector. 100 microliters of RT-300 was loaded in a 1 mL syringe with a 20 G×20 cm Chiba biopsy needle.

Transrectal or transperineal ultrasonography. Transrectal or transperineal prostate block with local anesthetic with 20 gauge syringe. Insertion of drug via the same 20 gauge needle into each lobe of the prostate. Positioning of the implanted medication confirmed by ultrasound. Removal of the ultrasound probe and needle.

Transrectal ultrasound was used to evaluate the size and condition of the prostate before and after treatment. Each animal received three injections of RT-300 (total dosage is 300 microliters) in the prostate under ultrasound guidance.

Animal #2000081

At the end of the procedure, animal #2000081 was humanely euthanized and sent to necropsy. For animal #2000081 the needle guide and biopsy needle were attached to the ultrasound rectal probe. The probe was advanced to the first prostate lobe. Prostate volume was measured to be 3.08 cm^3 via the equation:

$$\text{Prostate volume} = 0.5233 \times TRD \times APD \times LD$$

Where TRD was 1.83 cm, APD was 1.19 cm and LD was 2.70 cm.
(transverse diameter (TRD) anteroposterior diameter (APD), longitudinal diameter (LD))

FIG. 8 shows the transrectal ultrasound volume measurement of the canine prostate in animal #2000081. A 100 microliter of e-beam sterilized RT-300 was injected into the left prostate lobe as shown in FIG. 9. The probe was advanced to the second prostate lobe. 100 microliters of RT-300 was injected into the right prostate lobe. A second 100 microliter of e-beam sterilized RT-300 was injected into the right prostate lobe after the first injection was outside the lobe. The 200 microliters of RT-300 injectate can be visually seen as less than 10% of prostate volume under ultrasound.

The successful treatment is shown in FIG. 10.

FIG. 9 is an image showing treatment (injecting RT-300 into the prostate) that used a 20 G×20 cm Chiba biopsy needle.

FIG. 10 is an image showing the RT-300 injectable as visible in canine prostate.

After treatment with e-beam sterilized RT-300. The animal was humanely euthanized, and the prostate and surrounding bladder and urethra explanted. The RT-300 injections visibly observed in the explanted prostate, as shown in FIG. 11.

FIG. 12 indicates no significant adverse effects were observed due to the procedure or injectate.

Animal #2000083

For animal #2000083 (chronic model/animal), the needle guide and 20 G×20 cm Chiba biopsy needle was attached to the ultrasound rectal probe. The probe was advanced to the first prostate lobe. Prostate volume was measured to be 3.52 cm^3 via the equation:

$$\text{Prostate volume} = 0.5233 \times \text{TRD} \times \text{APD} \times \text{LD}$$

Where TRD was 1.88 cm, APD was 1.32 cm and LD was 2.71 cm (FIG. 13).

100 microliter of e-beam sterilized RT-300 was injected into the left prostate lobe. The probe was advanced to the second prostate lobe. 100 microliters of RT-300 was injected into the right prostate lobe. A second injection of 100 microliter of RT-300 was injected into the left prostate lobe after the first injection was outside the lobe. Prostate RT-300 injections were retained and visible in the prostate as observed under ultrasound (FIGS. 14-16). The animal recovered normally from anesthesia. The animal appeared bright, alert and comfortable, with slightly nervous temperament. The animal also had normal urine present in the pan liner the morning following the procedure.

Observations from Study

Figure 2:
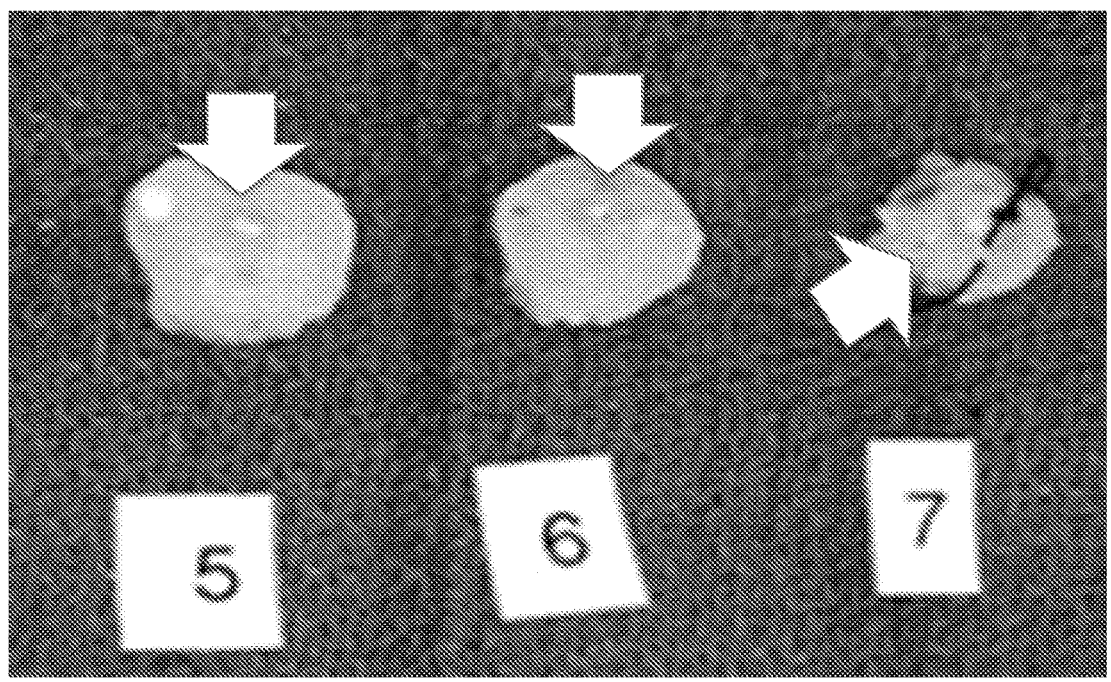
FIG. 2 shows gross pathology images of trimmed and formalin fixed treated prostate gland from a canine study acute animal 2000083. Visible white material demonstrates successful local injection of an SRF.

FIG. 2 shows gross pathology images of trimmed and formalin fixed treated prostate gland from a canine study acute animal 2000083. Visible white material demonstrates successful, localized injection of an SRF. These areas are identified by the white arrows in FIG. 2. The delivery vehicle (needle injection, the needle containing RT-300) is described above. The SRF localized to the areas shown indicates that the SRF had not undergone any significant diffusion into adjoining tissue, which is desired. The SRF was localized to the area where the injectate was placed.

Figure 3:
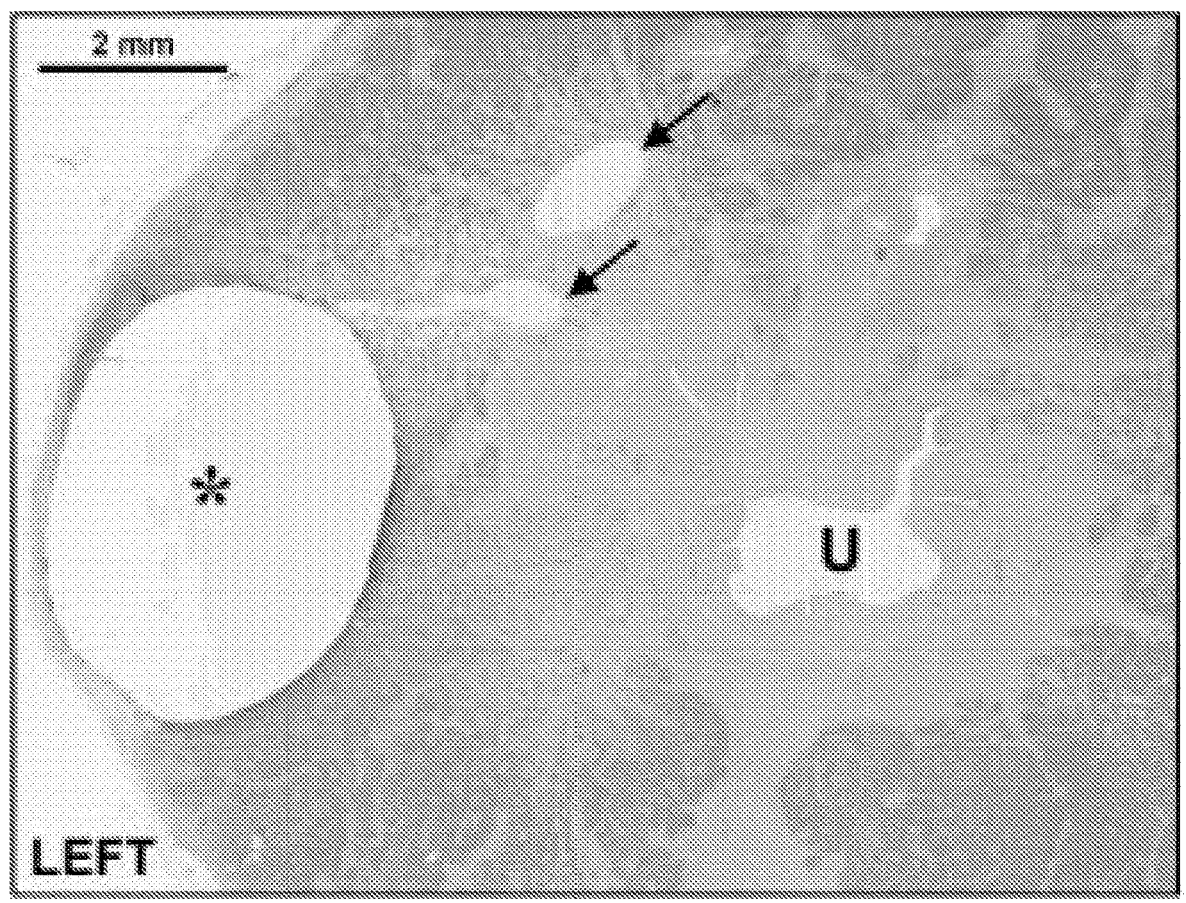
FIG. 3 shows an acute animal 2000083 treated prostate histopathology H&E stained image with poorly staining injectate material (containing the SRF) in the left lateral lobe (asterisk). (U=urethra, arrows designate needle tracks).

FIG. 3 shows an H&E (hematoxylin and eosin) stained histopathology image of a treated prostate from the acute animal 2000083 with poorly staining injectate material (identifying the presence of the SRF) in the left lateral lobe (asterisk). (U=urethra, arrows designate needle tracks). This image further indicates that the injectate, containing the SRF (RT-300), was localized without any significant diffusion into adjoining tissue for the acute animal. It is believed that without the SRF formulation of the drug and polymer there would have been significant diffusion of the cytotoxic drug, which is undesirable for at least two reasons. First, to treat the area effectively a higher wt % of drug injectate may be needed since the concentration of drug at the target tissue is reduced due to diffusion. Second, the drug, by diffusing to other areas may introduce adverse consequences. Hence it is desirable to minimize the amount of diffusion so that only the target tissue receives an effective amount of drug to treat the tissue.

Figure 4:
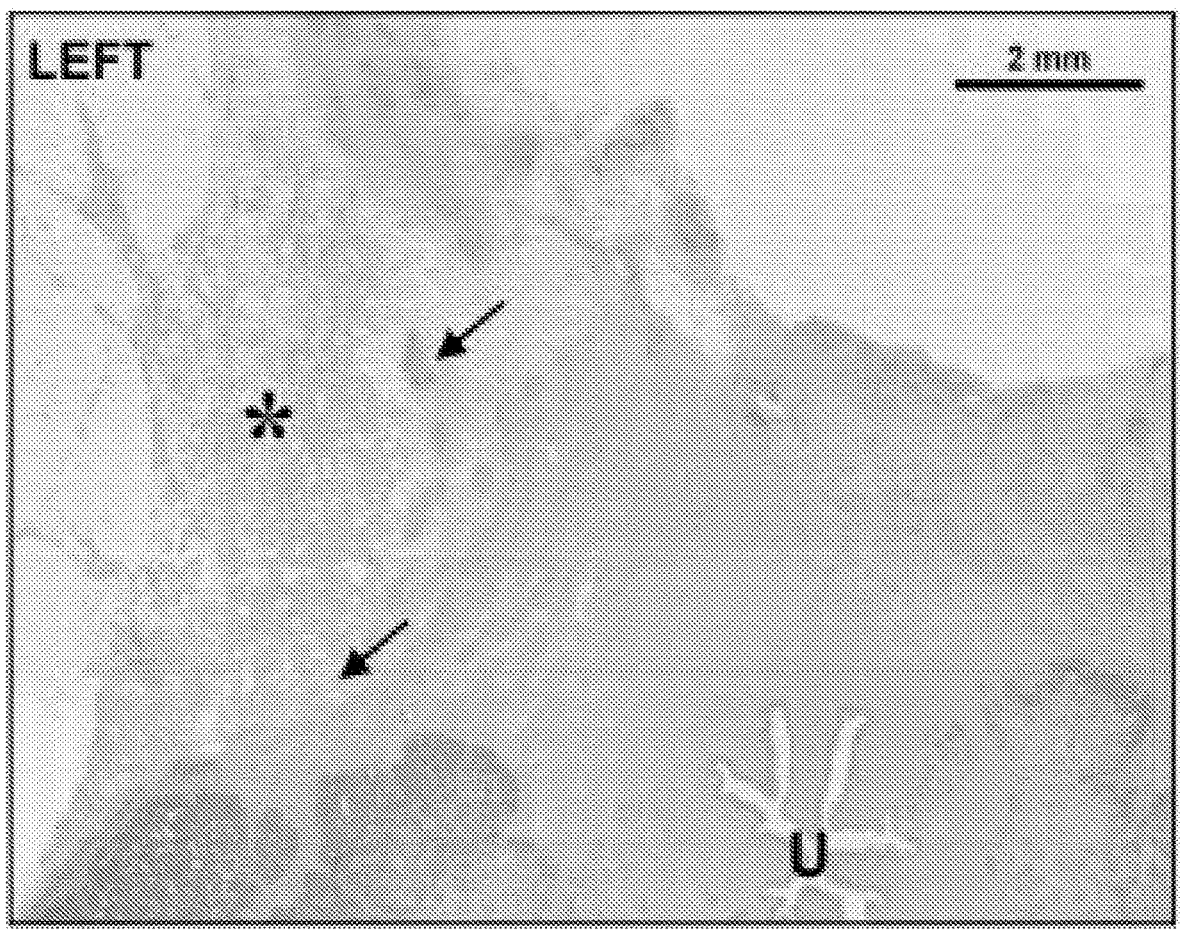
FIG. 4 shows a chronic 30-day animal 2000081 histopathology H&E stained image demonstrating degenerate smooth muscle in the left sided cranial prostate subsample (arrows). (U=urethra).

FIG. 4 shows a chronic 30-day animal 2000081 histopathology H&E stained image demonstrating degenerate smooth muscle in the left sided cranial prostate subsample (arrows). (U=urethra). It is believed that a key pathology of BPH is the proliferation of smooth muscle cell. The drug portion of the SRF is intended to degenerate smooth muscle cells or prevent their proliferation. The image shows that RT-300 was effective over a 30-day period in breaking down smooth muscle cells.

Figure 5:
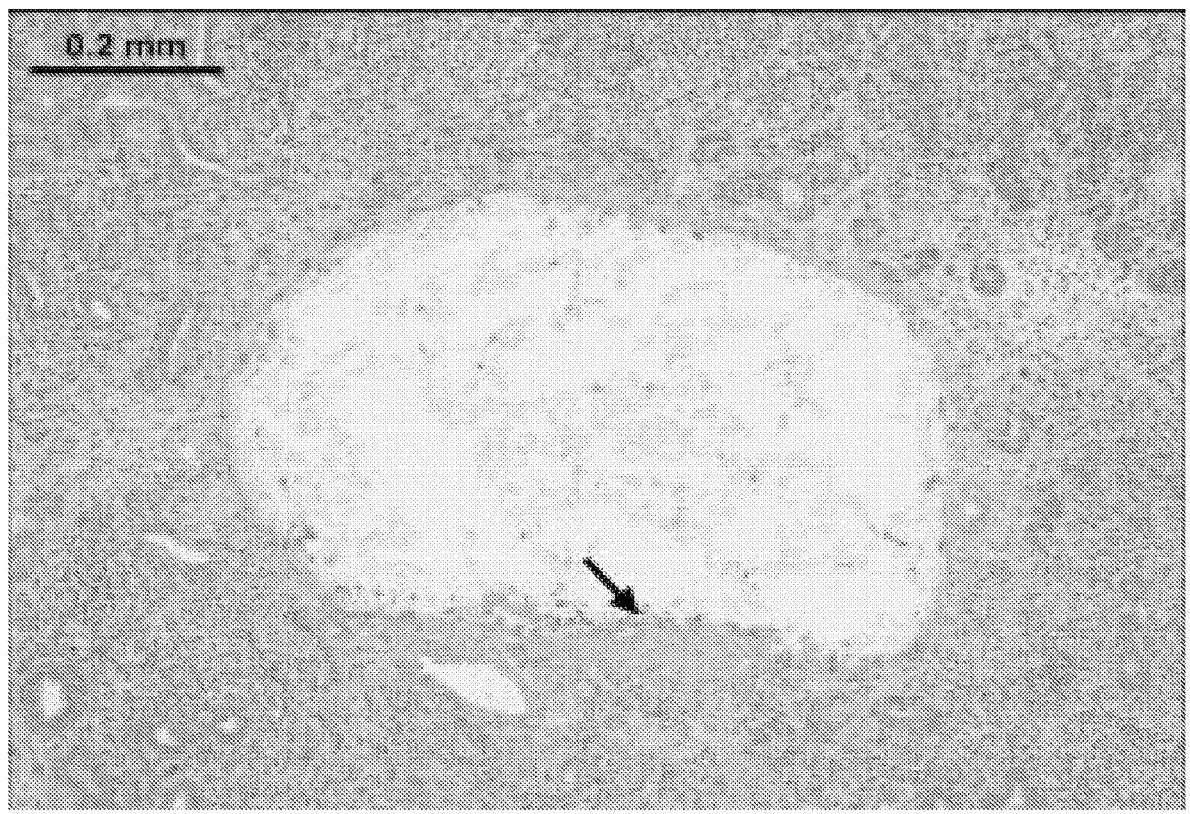
FIG. 5 shows a chronic 30-day animal 2000081 histopathology H&E stained image demonstrating prostate tissue surrounding injectate demonstrating loss of adjacent glandular acini adjacent (arrow).

FIG. 5 shows the chronic animal 2000081 histopathology H&E stained image demonstrating prostate tissue surrounding injectate and loss of adjacent glandular acini adjacent (arrow). The image indicating local loss of the glandular tissue evidence both drug effectiveness and desired treatment only at the target tissue.

Figure 6A:
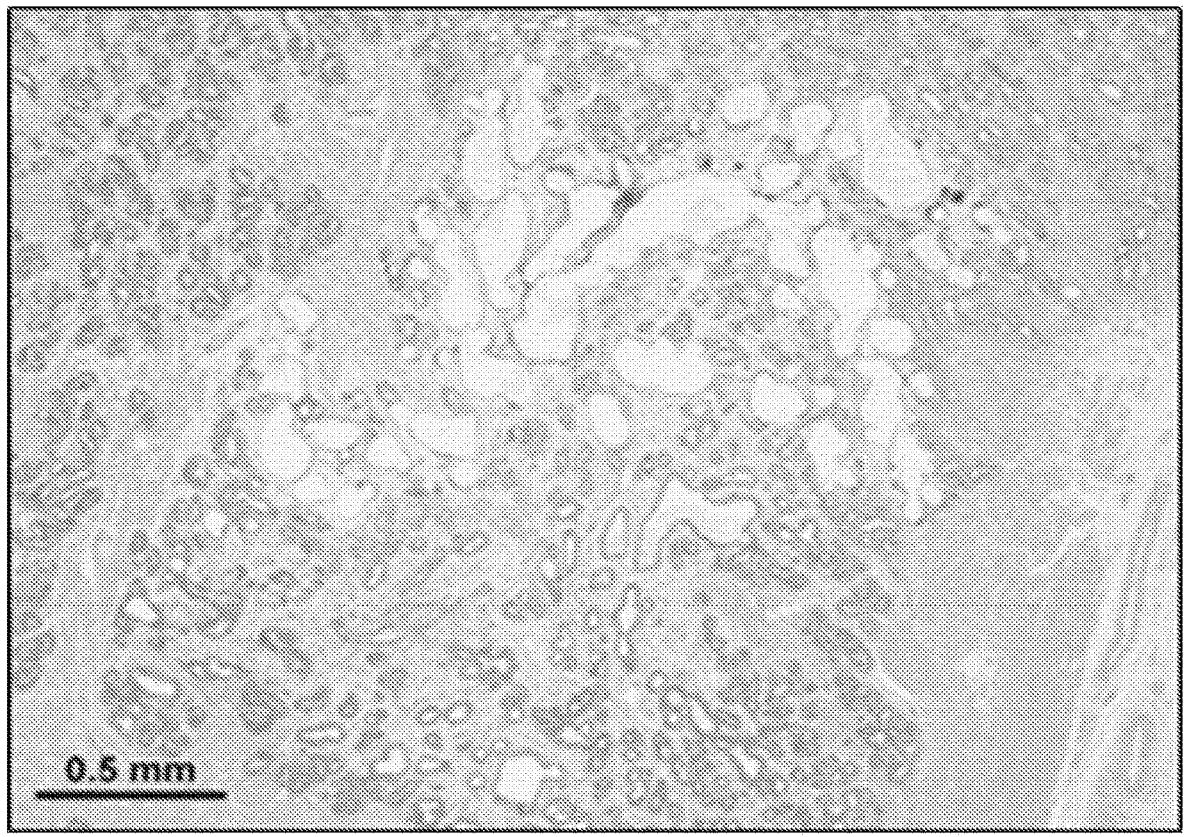
FIG. 6A shows glandular acini of the target tissue of the acute animal 2000083 (histopathology H&E stained).
Figure 6B:
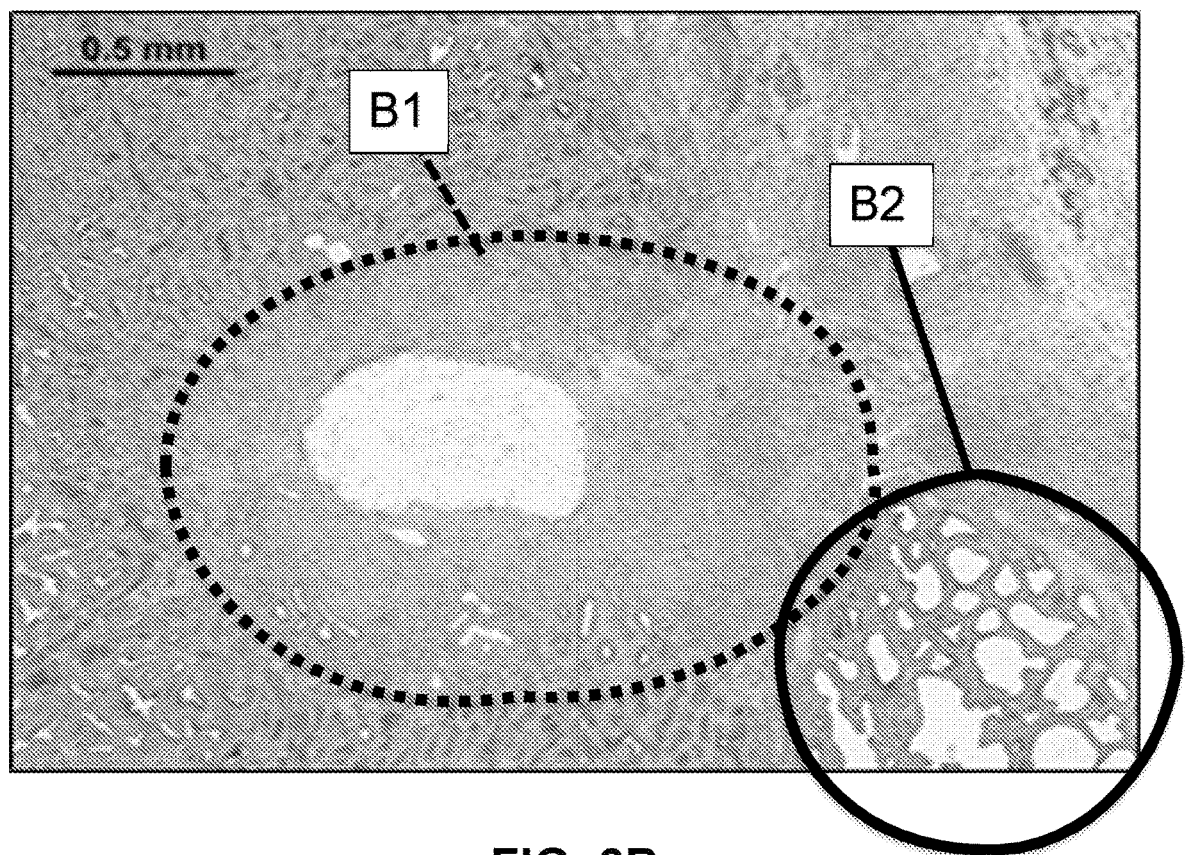
FIG. 6B shows the target tissue of the chronic 30-day animal 2000081 (Masson's trichrome stained). The white area in the image is the location where the SRF was injected into the target tissue. Comparing FIGS. 6A to 6B, there is a loss of the glandular acini in the 30-day animal versus shown in the acute animal (FIG. 6A). The circled area B2, which tissue image is similar to the tissue image in FIG. 6A, contrasts to tissue in B1, which is surrounding the SRF, and therefore has been impacted by the sustained release of the cytotoxic agent. This indicates the desired effect of the SRF on the target tissue over the 30-day period.
Figure 7:
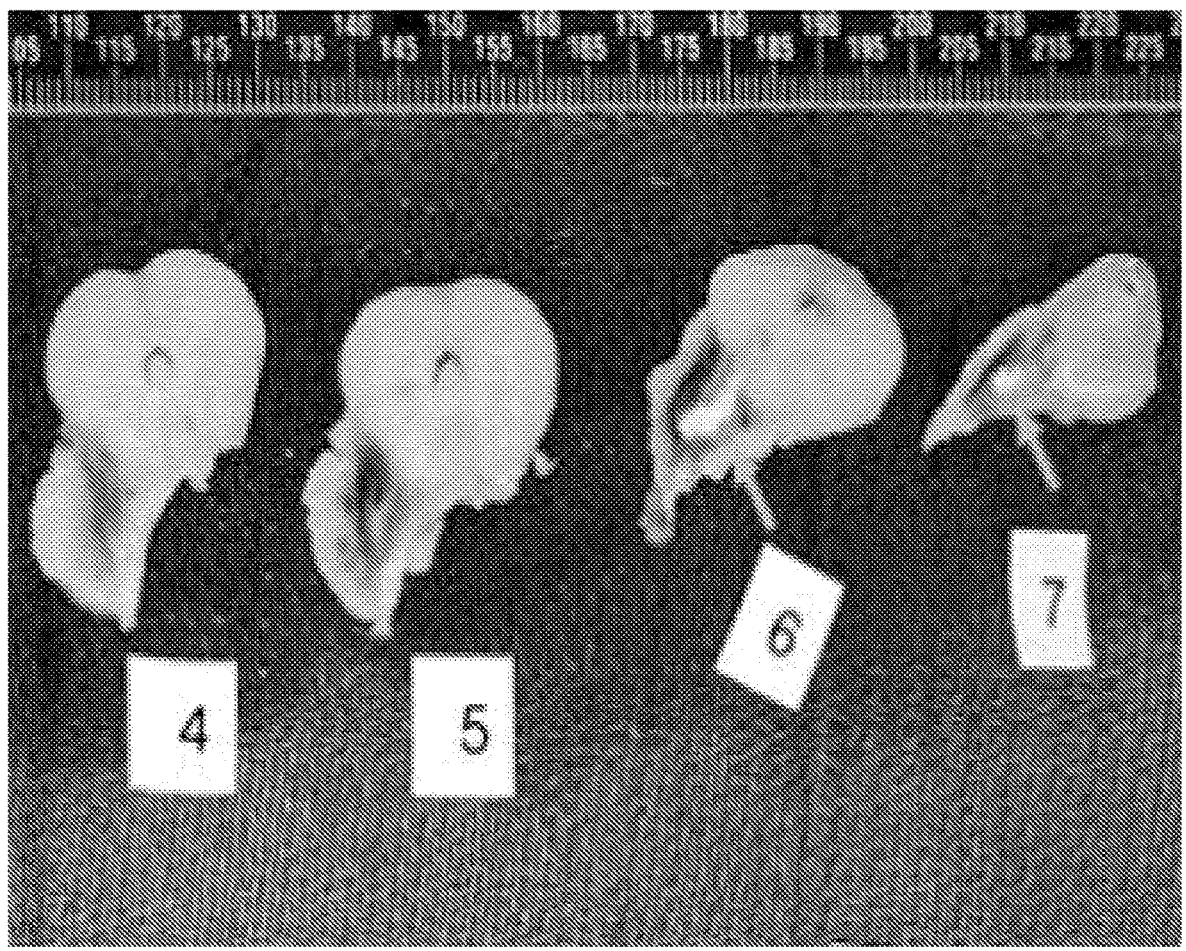
FIG. 7 is an image of target tissue of the chronic 30-day animal 2000081.

FIGS. 6A and 6B are comparison images that further evidence the effect of SRF after 30 days and its localized treatment, or lack of diffusion of the drug to tissue adjoining the target tissue or tissue nearby. FIG. 6A shows the target tissue morphology of the acute animal 2000083 (histopathology H&E stained). FIG. 6B shows the target tissue of the chronic animal 2000081 (Masson's trichrome stained). The white area in the image is the location of the target tissue where the SRF was injected. Comparing FIGS. 6A to 6B, there is a loss of the glandular acini shown in the acute animal (FIG. 6A). The circled area B2, which tissue image is similar to the tissue image in FIG. 6A, contrasts to the tissue identified in B1, which is surrounding the SRF. The SRF has impacted the tissue in the region of B1 by a sustained release of the cytotoxic agent. This image indicates that the desired effect of the SRF on the target tissue over the 30-day period has taken place. Additionally, this image indicates the lack of drug diffusion to nearby tissue, which is also desirable.

It will be appreciated by a person of ordinary skill, in view of the teachings in this disclosure and the observations from the study, that there is a capacity for effective treatment, localized to the treatment of BPH, and by a needle injection of a composition including a SRF at the target tissue, in contrast to other methods. While those other methods may show efficacy in reducing BPH, they either may require a more invasive procedure (vs. localized treatment using the delivery device as disclosed herein, such as the needle used in the animal study), more frequent treatment due to diffusion or more generalized treatment of BPH raising the possibility of adverse effects because a higher dosage is needed to treat the area while accounting for leakage or diffusion of the drug to other areas. Adverse effects may include diminished urinary or sexual function. It is desired to have an effective treatment targeting only the target tissue and nowhere else (e.g., avoiding the urethra) and to perform the procedure in a less invasive manner for patient acceptance. In contrast to other methods, a needle injection of the SRF at the target tissue, without significant diffusion, demonstrates a capacity to meet these objectives.

Following are additional listing of disclosed embodiments:

0.5 mL N-methyl pyrrolidone (NMP) was added to a vial with 0.25 g sirolimus and vortexed until dissolved. 50 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515E (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.3 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA8515E (0.7 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 200 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g sirolimus and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g sirolimus and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers. 0.5 mL N-methyl pyrrolidone (NMP) was added to a vial with 0.25 g everolimus and vortexed until dissolved. 50 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.7 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.5 dl/g) in NMP solution using syringe to syringe mixing with a female to female luer connector. 800 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.7 dl/g) in NMP solution using syringe to syringe mixing with a female to female luer connector. 800 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 100 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 200 microliter of drug solution was added to 2.5 mL of a 50% PLGA7525A (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525E (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525A (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525E (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525A (0.7 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA7525E (0.7 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535E (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535A (0.3 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535E (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535A (0.5 dl/g) in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535E (0.5 dl/g) in NMP solution using syringe to syringe mixing with a female to female luer connector. 500 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 200 microliter of drug solution was added to 2.5 mL of a 50% PLGA6535A (0.5 dl/g) in NMP solution using syringe to syringe mixing with a female to female luer connector. 500 microliters in a 1 mL syringe was loaded into a 20 G×20 cm Chiba biopsy needle with depth markers 0.5 mL N-methyl pyrrolidone (NMP) was added to a vial with 0.25 g everolimus and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g everolimus and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 50 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515E (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA8515A (0.7 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 500 microliter of drug solution was added to 2.5 mL of a 50% PLGA8515E (0.7 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 200 microliter of drug solution was added to 2.5 mL of a 50% PLGA8515 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 50 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 200 microliter of drug solution was added to 2.5 mL of a 50% PLGA7525 in NMP solution using syringe to syringe mixing with a female to female luer connector. 250 microliters in a 1 mL syringe was loaded into a 20 G×20 cm Chiba biopsy needle with depth markers 0.5 mL N-methyl pyrrolidone (NMP) was added to a vial with 0.25 g paclitaxel and vortexed until dissolved. 100 microliter of drug solution was added to 2.5 mL of a 50% PLGA6535A (0.3 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA6535A (0.5 dl/g) in NMP solution using syringe to syringe mixing with a female to female luer connector. 500 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 500 microliter of drug solution was added to 2.5 mL of a 50% PLGA6535E (0.3 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 500 microliter of drug solution was added to 2.5 mL of a 50% PLGA6535E (0.5 dl/g) in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 50 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 100 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

0.5 mL N-methyl pyrrolidone (NMP) was added to a vial with 0.25 g paclitaxel and vortexed until dissolved. 200 microliter of drug solution was added to 2.5 mL of a 50% PLGA5050 in NMP solution using syringe to syringe mixing with a female to female luer connector. 250 microliters in a 1 mL syringe was loaded into a 20 G×20 cm Chiba biopsy needle with depth markers.

Additional aspects of the disclosure are set forth in the Embodiments E1-E39 set forth below:

E1. A system for treatment of benign prostatic hyperplasia tissue, comprising: a sustained release formulation (SRF) comprising a cytostatic or cytotoxic drug, and an applicator or delivery system for local delivery of a composition comprising or consisting essentially of the SRF to the target tissue of the prostate.

E2. The system of E1 or any claim depending from E1, wherein the SRF is adapted to release the drug into the prostate over at least 14 days from being injected into the prostate, or over a 30 to 90 day period, or over a 90 to 180 day period.

E3. The system of E1 or any claim depending from Claim E1, wherein the composition includes a solvent and the sustained release formulation.

E4. The system of E1 or any claim depending from Claim E1, wherein the cytostatic drug consists of rapamycin, sirolimus, everolimus, temsirolimus, or zotarolimus.

E5. The system of E1 or any claim depending from Claim E1, where the cytotoxic drug consists of paclitaxel.

E6. The system of E1 or any claim depending from E1, wherein the composition is an injectable solution and the sustained release formulation is formed into one or more of, or any of combination of microparticles, nanoparticles, rods, or a gel when the sustained release formulation comes into contact with the prostate.

E7. The system of E1 or any claim depending from E1, wherein the composition is an injectable solution and the sustained release formulation forms into one or more of, or any of combination of microparticles, nanoparticles, rods, or a gel.

E8. The system of E1 or any claim depending from E1, where the sustained release formulation is bioabsorbable and comprises a glycolide-based copolymer; optionally poly (lactide-co-glycolide).

E9. The system of E1 or any claim depending from E1, where the applicator comprises a needle for delivery of the composition by a transurethral, transrectal or transperineal access.

E10. The system of E1 or any claim depending from E1, wherein the system further includes an ultrasound device for locating a target in the prostate.

E11. A system for treatment of benign prostatic hyperplasia tissue, comprising: a sustained release formulation comprising an alpha blocker, and/or a 5-alpha reductase inhibitor, and an applicator or delivery system for local delivery of a composition comprising or consisting essentially of the sustained release formulation to the prostate.

E12. The system of E1 or any claim depending from E1, wherein the composition further comprising an anti-inflammatory, alpha blocker, or a 5-alpha reductase inhibitor.

E13. The system of E1 or any claim depending from E1, wherein the composition further comprising an anti-inflammatory corticosteroid for sustained exposure and the corticosteroid includes dexamethasone, budesonide, mometasone furoate, triamcinolone acetonide, fluticasone propionate, or fluticasone furoate.

E14. The system of E1 or any claim depending from E1, wherein the composition comprises a bioabsorbable polymer at a concentration of 20-80%, 25-75%, 40-60% by wt. of the bioabsorbable polymer, 80-20%, 75-25%, 60-40%, by wt. of the solvent and 0.5%-30% by wt. drug; 1%-20% by wt. of drug, or 1%-5% by wt. of drug.

E15. The system of E1 or any claim depending from E1, wherein the drug has a release rate of no more than 10% to 75% over the first month, 25% to 95% over the first three months, and/or 50% to 100% over the first six months.

E16. The system of E1 or any claim depending from E1, wherein the drug has a release rate of between 5% to 50% during the first 24 hours from injecting the composition into the prostate.

E17. The system of E1 or any claim depending from E1, wherein the composition comprises a bioabsorbable polymer and the inherent viscosity of the polymer is between 0.2-1.0 dL/g, 0.2-0.6 dL/g, or 0.2 to 0.4 dL/g or 0.2 to 0.3 dL/g and the ratio of DL-lactide to glycolide is from 50/50 up to 90/10, 95/5, or 85/15.

E18. The system of E1 or any claim depending from E1, wherein the cytostatic or cytotoxic drug is 0.1 up to 10% wt. or up 20-30% wt. of the sustained release formulation.

E19. The system of E1 or any claim depending from E1, wherein the solvent is water soluble and non-toxic, and the composition comprises a polymer that is soluble in the solvent.

E20. The system of E1 or any claim depending from E1, wherein the solvent is water soluble or not water soluble, non-toxic, and/or the cytostatic or cytotoxic drug is soluble in in the solvent.

E21. The system of E1 or any claim depending from E1, wherein the solvent comprises N-methyl-pyrrolidone.

E22. The system of E1 or any claim depending from E1, wherein the composition comprises a polymer and the polymer is poly(DL-lactide).

E23. A method of treatment using the system of E1 or any claim depending from E1, comprising: injecting the composition into the prostate.

E24. The method of E23, or any claim depending from E23, wherein the cytostatic drug comprises rapamycin, sirolimus, everolimus, temsirolimus, or zotarolimus.

E25. The method of E23 or any claim depending from E23, wherein the cytotoxic drug comprises paclitaxel.

E26. The method of E23 or any claim depending from E23, wherein the composition is injected into the prostate and upon reaching the prostate the sustained release formulation forms into one or more of, or any of combination of microparticles, nanoparticles, rods, or a gel when the sustained release formulation comes into contact with the prostate.

E27. The method of E23 or any claim depending from E23, wherein the sustained release formulation comprises poly(lactide-co-glycolide).

E28. The method of E23 or any claim depending from E23, wherein the applicator comprises a needle for delivery of the composition, and the method includes delivering the composition by a transurethral, transrectal or transperineal access.

E29. The method of E23 or any claim depending from E23, wherein the composition is injected using a needle having 16 or higher gauge needle and the needle has a length of between 10 cm and 40 cm.

E30. The method of E23 or any claim depending from E23, wherein upon implanting the composition into the prostate the composition retains as a solid or gel implant and provides sustained release of the drug; the water soluble solvent mixing with hydrophilic tissue fluids and leaving or precipitating the remaining drug and polymer as a solid implant.

E31. The method of E23 or any claim depending from E23, wherein the composition comprising the polymer is selected from the set of poly(lactide-co-glycolide), poly(D,L-lactide-co-glycolide), poly(D,L-lactide-co-glycolide) (50-50), poly(D,L-lactide-co-glycolide (75-25), poly(D,L-lactide-co-glycolide (85-15), poly(D,L-lactide), ester end capped poly(D,L-lactide-co-glycolide), acid end capped poly(D,L-lactide-co-glycolide), or some combination thereof:

E32. The method of E23 or any claim depending from E23, wherein the injection is made through the transurethral, transrectal and/or transperineal areas of the prostate.

E33. The method of E23 or any claim depending from E23, wherein the injecting the composition forms a gel or foam when placed in contact with the prostate.

E34. The method of E23 or any claim depending from E23, wherein the injecting includes an ultrasound device for locating a target in the prostate.

E35. The method of E23 or any claim depending from E23, wherein the injectate and/or applicator are visible under ultrasound imaging.

E36. The method of E23 or any claim depending from E23, wherein the composition retains the drug localized to the prostate tissue hyperplasia and prevents undesirable destruction of surrounding tissues.

E37. The system of E1 or any claim depending from E1, wherein the composition retains the drug localized to the prostate tissue hyperplasia and prevents undesirable destruction of surrounding tissues.

E38. The system of E1 or any claim depending from E1, wherein the composition volume consists of 1% to 25% of the prostate volume or 5% to 15% of the prostate volume.

E39. The system of E1 or any claim depending from E1, wherein the composition biodegrades in a time frame of 3 to 6 months or 6 to 12 months.

The invention claimed is:

1. A method of treatment for benign prostatic hyperplasia (BPH), comprising the steps of:
   using a needle syringe containing a composition; and
   dispensing a plurality of doses of the composition into a prostate at a respective plurality of locations within the prostate using the needle syringe;
   wherein the composition comprises:
      a cytotoxic drug, wherein the cytotoxic drug is paclitaxel;
      a glycolide-based bioabsorbable copolymer selected from the group consisting of poly(D,L-lactide-co-glycolide) (50:50), poly(D,L-lactide-co-glycolide) (65:35), poly(D,L-lactide-co-glycolide) (75:25), and poly(D,L-lactide-co-glycolide) (85:15); and
      a water-soluble solvent capable of dissolving the cytotoxic drug and glycolide-based bioabsorbable copolymer;
   wherein the water-soluble solvent capable of dissolving the cytotoxic drug and glycolide-based bioabsorbable copolymer is selected from the group consisting of N-methylpyrrolidone (NMP) and dimethyl sulfoxide (DMSO); and
   wherein the dispensing a plurality of doses comprises consecutively dispensing at least a first dose of the composition into a first location, and a second dose of the composition into a second location within the prostate using the needle syringe.

2. The method of claim 1, wherein the dose comprises 100 microliters of the composition.

3. The method of claim 1, wherein the water-soluble solvent capable of dissolving the cytotoxic drug and glycolide-based bioabsorbable copolymer is NMP.

4. The method of claim 1, wherein the cytotoxic drug has a total concentration of 0.5-30 wt % of the composition.

5. The method of claim 1, comprising releasing the composition comprising the cytotoxic drug into the prostate over at least 14 days from being injected into the prostate.

6. The method of claim 1, wherein the cytotoxic drug has a release rate of no more than 10% to 75% over the first month.

7. The method of claim 1, wherein the cytotoxic drug has a release rate of between 5% to 50% during the first 24 hours from injecting the composition into the prostate.

8. The method of claim 1, wherein the glycolide-based bioabsorbable copolymer has a viscosity between 0.2-0.6 dL/g.

9. The method of claim 4, wherein the cytotoxic drug is 0.1 to 10 wt % of the composition.

10. The method of claim 1, wherein the water-soluble solvent comprises N-methyl-pyrrolidone, the cytotoxic drug is paclitaxel and the glycolide-based bioabsorbable polymer is poly(D,L-lactide-co-glycolide) (85:15).

11. A method of treatment for benign prostatic hyperplasia (BPH), comprising the steps of:
   using a needle syringe containing a composition; and
   dispensing a plurality of doses of the composition into a prostate at a respective plurality of locations within the prostate using the needle syringe;
   wherein the composition comprises
      a cytostatic drug selected from the group consisting of sirolimus and everolimus;
      a glycolide-based bioabsorbable copolymer selected from the group consisting of poly(D,L-lactide-co-glycolide) (50:50), poly(D,L-lactide-co-glycolide) (65:35), poly(D,L-lactide-co-glycolide) (75:25), and poly(D,L-lactide-co-glycolide) (85:15); and
      a water-soluble solvent capable of dissolving the cytostatic drug and glycolide-based bioabsorbable copolymer;
   wherein the water-soluble solvent capable of dissolving the cytostatic drug and glycolide-based bioabsorbable copolymer is selected from the group consisting of N-methylpyrrolidone (NMP) and dimethyl sulfoxide (DMSO); and
   wherein the dispensing a plurality of doses comprises consecutively dispensing at least a first dose of the composition into a first location, and a second dose of the composition into a second location within the prostate using the needle syringe.

12. The method of claim 11, wherein the cytostatic drug is 0.1 to 10 wt % of the composition.

13. The method of claim 12, wherein the water-soluble solvent comprises N-methyl-pyrrolidone, the cytostatic drug is sirolimus and the glycolide-based bioabsorbable copolymer is poly(D,L-lactide-co-glycolide) (85:15).

14. The method of claim 12, wherein the cytostatic drug is sirolimus.

15. The method of claim 1, the cytotoxic drug has a total concentration of 1-20 wt % of the composition.

16. The method of claim 15, wherein the cytotoxic drug has a total concentration of 2-6 wt % of the composition.

17. The method of claim 1, wherein the cytotoxic drug has a release rate of no more than 25% to 95% over the first three months.

18. The method of claim 1, wherein the cytotoxic drug has a release rate of no more than 50% to 100% over the first six months.

19. The method of claim 4, wherein the cytotoxic drug is 20-30 wt % of the composition.

20. The method of claim 11, wherein the cytostatic drug is 20-30 wt % of the composition.

21. The method of claim 1, comprising releasing the cytotoxic drug into the prostate over a 30 to 90 day period.

22. The method of claim 1, comprising releasing the cytotoxic drug into the prostate over a 90 to 180 day period.

23. The method of claim 1, wherein the glycolide-based bioabsorbable copolymer has a viscosity between 0.2 to 0.4 dL/g.

24. The method of claim 23, wherein the glycolide-based bioabsorbable copolymer has a viscosity between 0.2 to 0.3 dL/g.

* * * * *